United States Patent
Toda et al.

[11] Patent Number: 5,897,509
[45] Date of Patent: Apr. 27, 1999

[54] PROBE FOR MEASURING PERIODONTAL POCKET DEPTH

[75] Inventors: Masataka Toda, Toyohashi; Hiroyuki Suganuma, Nagoya; Shiro Yamazaki, Anjo; Koji Kuno, Nagoya, all of Japan

[73] Assignee: Aisin Seiki Kabushiki Kaisha, Kariya, Japan

[21] Appl. No.: 08/880,677

[22] Filed: Jun. 23, 1997

[30] Foreign Application Priority Data

Jun. 21, 1996 [JP] Japan .................................. 8-161989
Jun. 21, 1996 [JP] Japan .................................. 8-161990
Jun. 27, 1996 [JP] Japan .................................. 8-167840
Jun. 27, 1996 [JP] Japan .................................. 8-167841
Mar. 28, 1997 [JP] Japan .................................... 9-78054

[51] Int. Cl.$^6$ .................................................. A61B 5/103
[52] U.S. Cl. ........................... 600/589; 600/590; 433/29; 33/514
[58] Field of Search .................................. 600/587, 589, 600/590, 595; 433/29, 72, 75; 33/513, 514

[56] References Cited

U.S. PATENT DOCUMENTS

| | | | |
|---|---|---|---|
| 4,677,756 | 7/1987 | Simon et al. ........................... | 600/589 |
| 4,764,114 | 8/1988 | Jeffcoat et al. ........................ | 600/589 |
| 4,791,940 | 12/1988 | Hirschfeld et al. .................... | 600/590 |
| 5,022,856 | 6/1991 | Zimble .................................... | 600/589 |
| 5,197,487 | 3/1993 | Ackerman et al. ..................... | 600/589 |
| 5,570,182 | 10/1996 | Nathel et al. ........................... | 356/345 |
| 5,755,571 | 5/1998 | Companion ............................. | 433/72 |

FOREIGN PATENT DOCUMENTS 0 253 812   1/1988   European Pat. Off. .

*Primary Examiner*—Max Hindenburg
*Assistant Examiner*—Charles Marmor, II
*Attorney, Agent, or Firm*—Oblon, Spivak, McClelland, Maier & Neustadt, P.C.

[57] ABSTRACT

A probe for measuring a depth of a periodontal pocket includes an emitting device for emitting, from a position at a distance from the periodontal pocket, a light beam toward the periodontal pocket, a receiving device for receiving, at a position at another distance from the periodontal pocket, the light beam after being reflected on a bottom of the periodontal pocket, and an analyzing device for displaying the depth of the periodontal pocket after a calculation thereof on the basis of an analysis of the light beam received at the receiving device.

11 Claims, 27 Drawing Sheets

(A)          (B)

Fig. 31
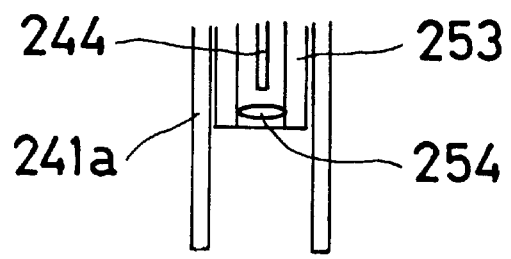
Fig. 32
(A)
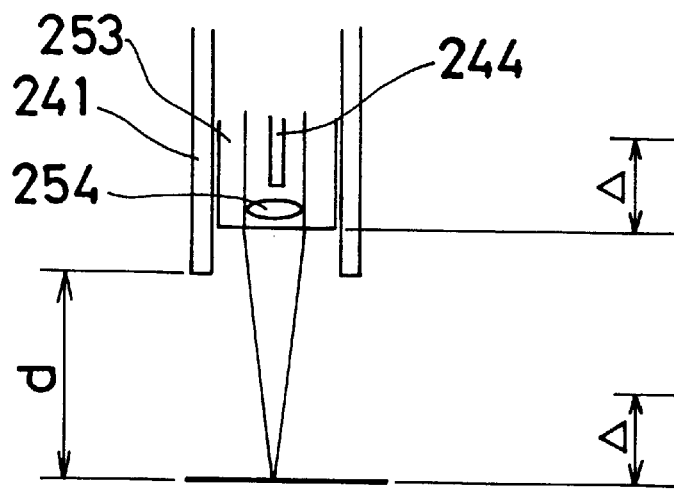
(B)
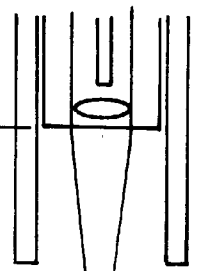

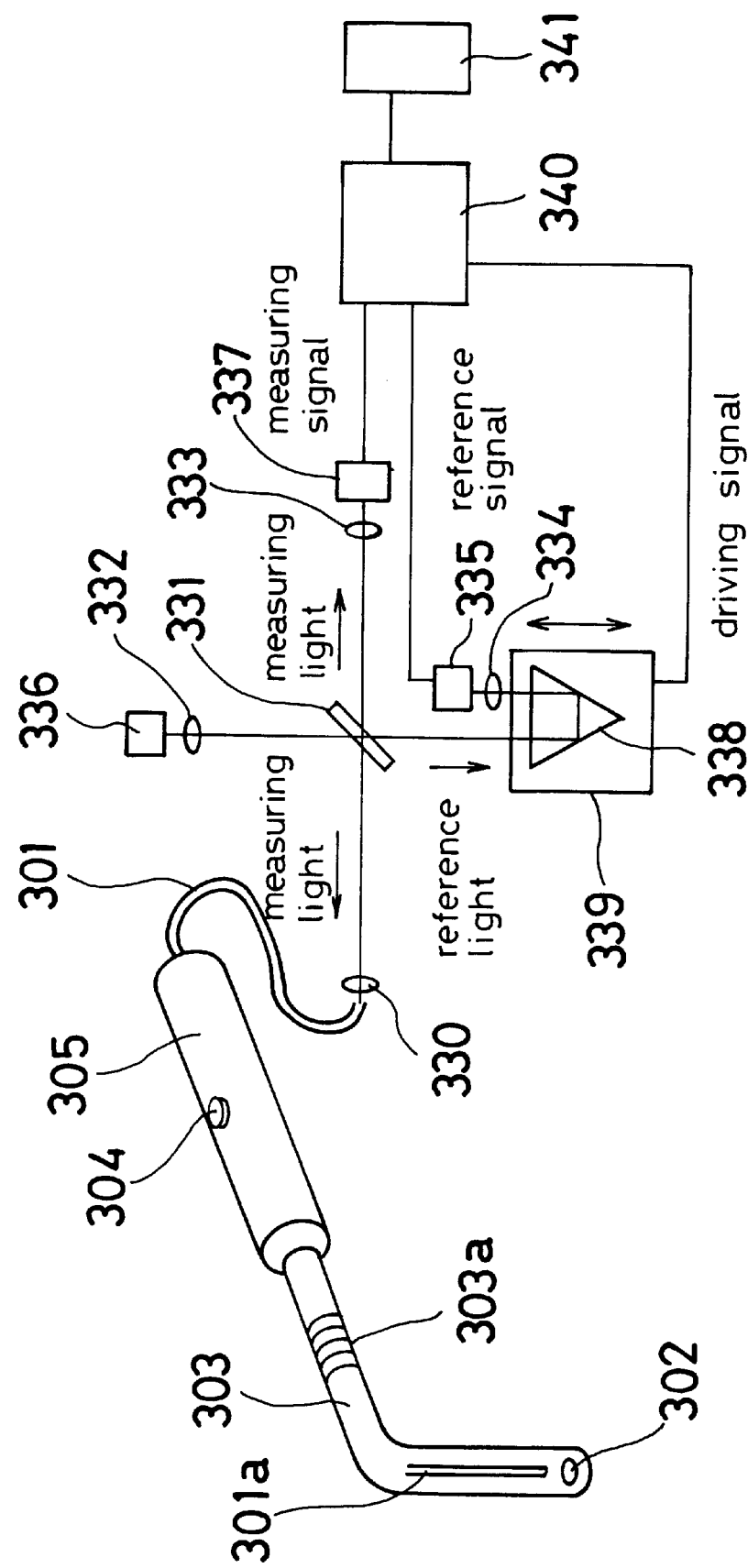

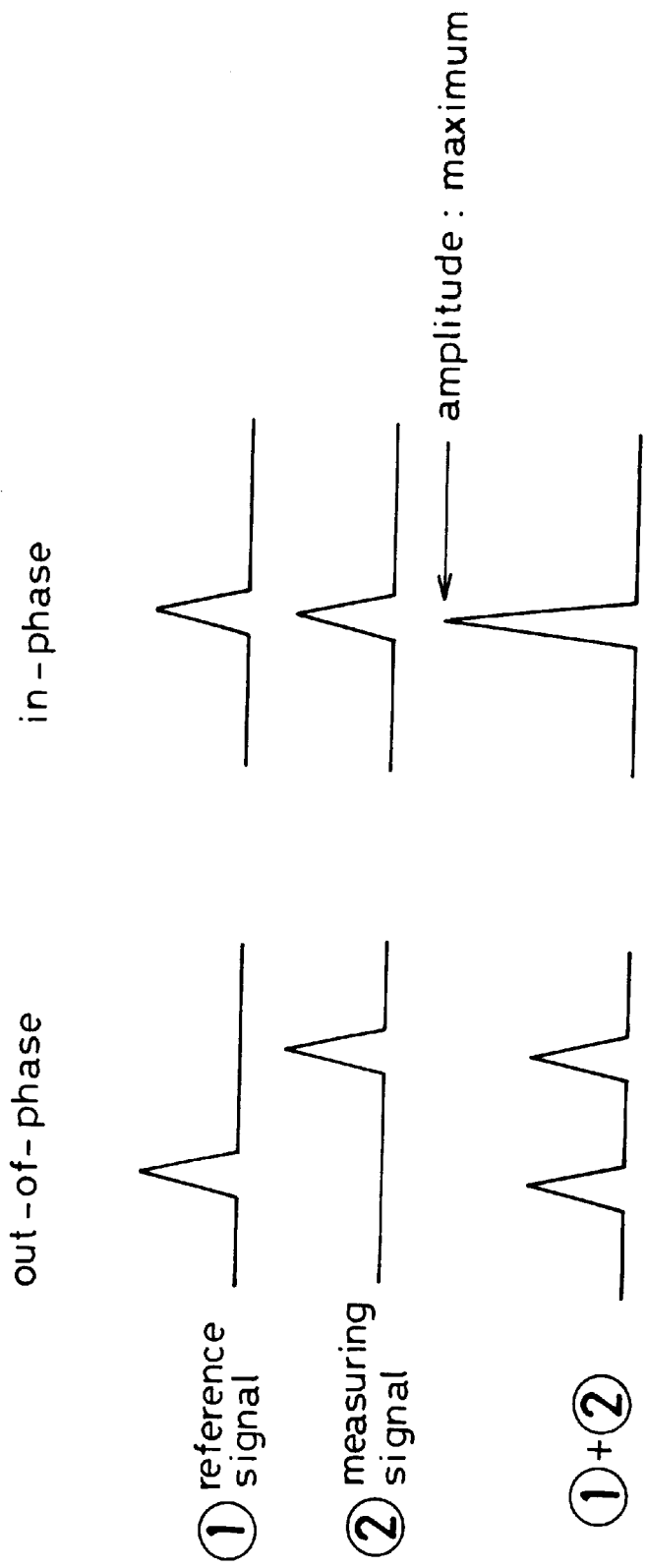

PROBE FOR MEASURING PERIODONTAL POCKET DEPTH

BACKGROUND OF THE INVENTION

1. Field of the Invention

The present invention relates to a probe for measuring the periodontal pocket and, in particular to a probe which can establish such a measurement without being engaged with a gum.

2. Description of the Related Art

It is well known that before diagnosing periodontal disease, the depth of the periodontal pocket along an outer surface of a tooth has to be measured. For measuring the depth, a mechanical dental probe is used. One of the conventional probes is disclosed in the U.S. Pat. No. 4,791,940. This probe includes a tip. When the tip rests on the bottom of the periodontal pocket after an insertion of the probe into the periodontal pocket, the tip is locked and the exposed length of the tip is measured for representing the depth of the periodontal pocket.

However, in the aforementioned measurement using the conventional probe, during the insertion of the tip of the probe into the periodontal pocket the dentist or technician slides the tip along the outer surface of the tooth from one location to another without withdrawing the tip unless the patient complains about discomfort or the pain.

Thus, determining the depth of the periodontal pocket often cannot be established without the patient's complaint or pain.

SUMMARY OF THE INVENTION

It is, therefore, a principal object of the present invention is to provide a probe without the foregoing drawback.

In order to attain the foregoing object, a probe for measuring the depth of a periodontal pocket includes emitting means for emitting, from a position at a distance from the periodontal pocket, a light beam toward the periodontal pocket; receiving means for receiving, at a position at another distance from the periodontal pocket, the light beam after being affected at the periodontal pocket, and analyzing means for calculating the depth of the periodontal pocket on the basis of an analysis of the light beam received at the receiving means.

BRIEF DESCRIPTION OF THE DRAWINGS

The above and other objects, features and advantages of the present invention will be more apparent and more readily appreciated from the following detailed description of a preferred exemplary embodiment of the present invention, taken in connection with the accompanying drawings, in which;

FIG. 31 is an enlarged cross-sectional view of portion C in FIG. 30;

FIG. 32 shows how the depth of the periodontal pocket can be measured by using the probe shown in FIG. 30;

FIG. 41 is a diagram of another modification of the probe shown in FIG. 35; and

FIG. 42 shows how a depth of the periodontal pocket can be measured by using the probe shown in FIG. 41.

DESCRIPTION OF THE PREFERRED EMBODIMENTS

Figure 1:
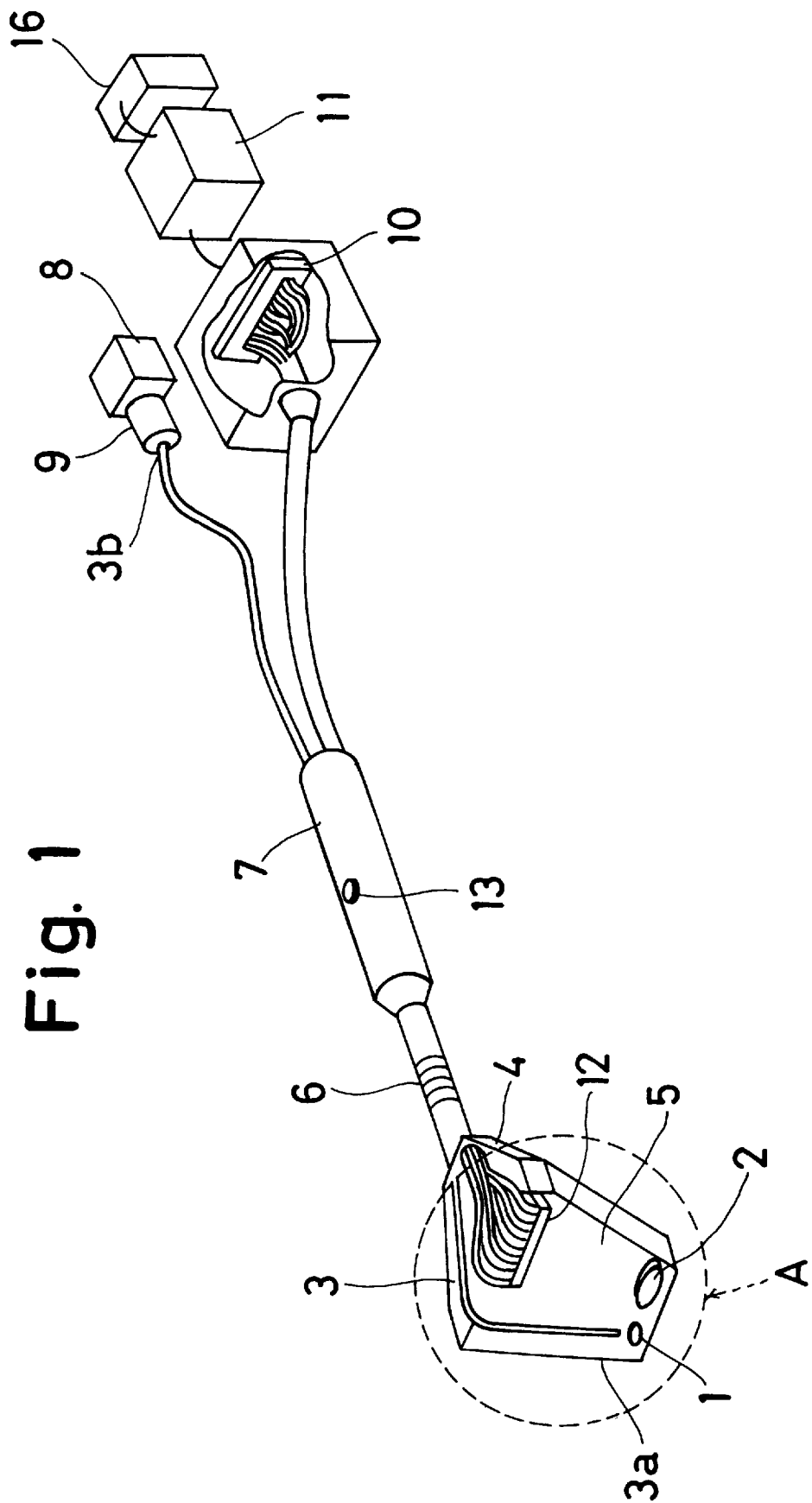
FIG. 1 is a diagram of a first embodiment of a probe according to the present invention.
Figure 2:
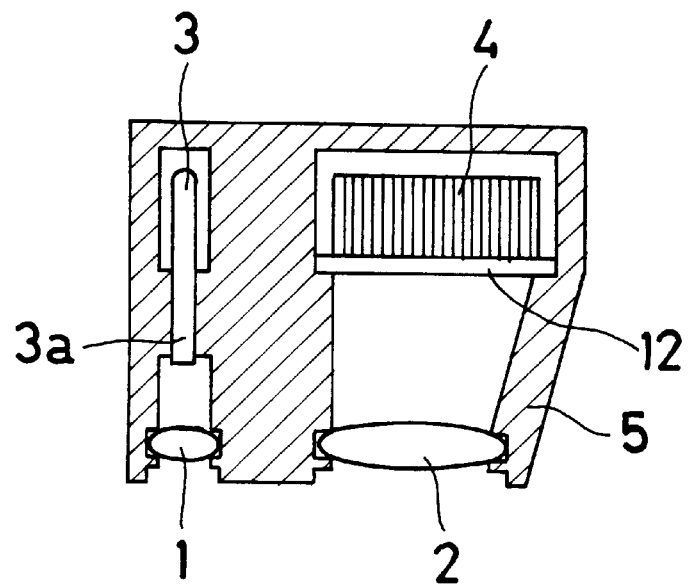
FIG. 2 is an enlarged view of portion A in FIG. 1.
Figure 3:
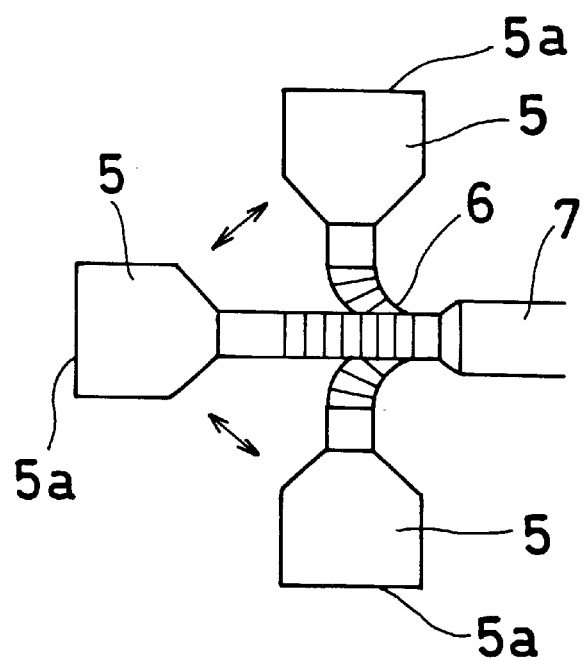
FIG. 3 is a view showing movements of a head portion of the probe shown in FIG. 1.
Figure 4:
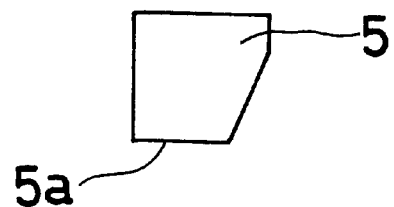
FIG. 4 is a side view of the head portion.

Preferred embodiments of the present invention will be described hereinafter in detail with reference to the accompanying drawings.

First Embodiment

Referring first to FIGS. 1 through 6, there is illustrated a probe or apparatus which is designed for measuring the depth of a periodontal pocket 32, includes a head portion 5.

At a distal end or lower end of the head portion 5 there are provided a first lens 1 and a second lens 2 in a side-by-side relationship. A proximal or upper end of the head portion 5 is connected, via a flexible tube 6 which is in the form of a goose neck, to an elongated handle portion 7, with the result that (FIG. 3) the head portion 5 can make a desired angle relative to the handle portion 7. In addition, as can be seen from FIG. 4, a bottom surface 5a of the head portion 5 is formed into a flat configuration so as to be used for a reference level which will be detailed later.

A left end portion 3a of an optical fiber 3 is extended into the head portion 5 after passing through the handle portion 7 and the flexible tube 6, and is in close opposition to the first lens 1. On the other hand, a right end portion 3b of the optical fiber 3 is positioned to receive a laser beam via a collecting lens 9 from a laser beam emission source 8 when a switch 13 which is provided to an outer surface of the handle portion is turned on.

A bundle of optical fibers 4 are passed through the handle portion 7 and the flexible tube 6. A left end of each of the optical fiber 4 is connected to a common transparent flat plate 12 within the head portion 5. The plate 12 is located at distance from the second lens 2 and is in opposition thereto. A right end of each optical fiber 4 is connected to a data or image processor 11 which is in the form of a microcomputer, via a linear image sensor 10. Thus, the beam from optical fiber 3, after being reflected on a bottom 32a of a periodontal pocket 32 (FIG. 6), is received at the second lens 2 and the resulting beam is transmitted, via the plate 12, the optical fibers 4 and the linear image sensor 10, to the image processor 11 to be processed thereat.

Figure 5:
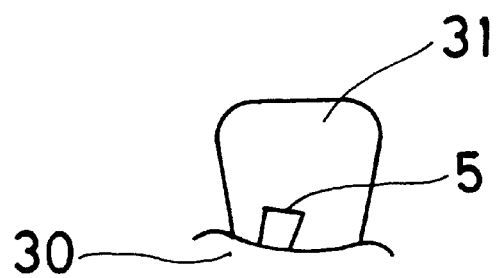
FIG. 5 is a front view showing how the head portion is set when the probe is used.
Figure 6:
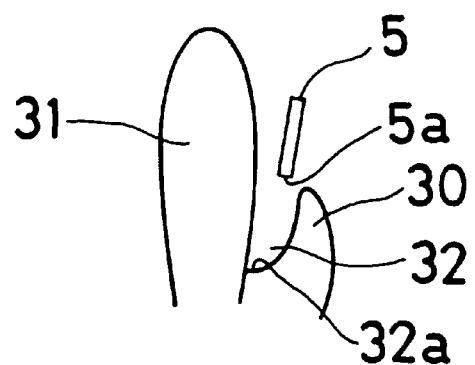
FIG. 6 is a side cross-sectional view showing how the head portion is set when the probe is used.

In operation, as shown in FIGS. 5 and 6, the handle portion 7 is held by a dentist or a technician (neither is shown) in such manner that the bottom 5a of the head portion 5, which is used as the measuring criteria, is brought into an out-of-contact coincidence relationship with a gum line of a gum 30 and the head portion 5 is oriented to the bottom 32a of the periodontal pocket 32 between an outer surface of a tooth 31 and an inner surface of the gum 30. Thereafter, when the switch 13 is turned on, the laser beam is emitted from the laser beam emission source 8 and illuminates only a small area on the bottom 32a of the periodontal pocket 32. Then, the beam is reflected at the bottom 32a of the periodontal pocket 32, and the resulting or reflected beam is transmitted to the linear image sensor 10 via the second lens 2, the plate 12 and the optical fibers 4. At the linear image sensor 10, the reflected beam is converted into an electric signal in the form of electric pulses. Such a signal is fed to the linear image processor 11 and is calculated or manipulated therein on the basis of triangulation, as will be detailed later, for determining the depth of the periodontal pocket 32. The determined depth or the resultant value is then digitally displayed on a numeric display or CRT 16.

Figure 9:
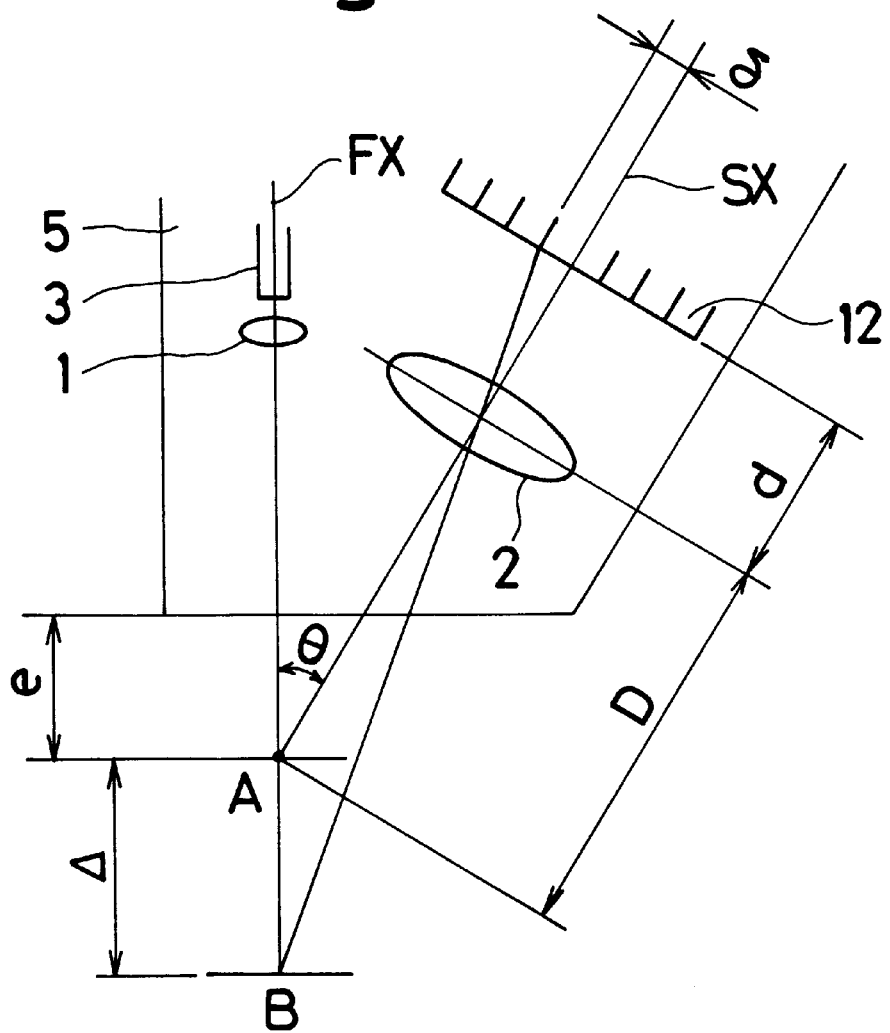
FIG. 9 shows how the depth of the periodontal pocket is determined using triangulation.

Hereinafter, the triangulation principle will be explained in detail. FIG. 9 illustrates a relationship between the head portion 5, a position 'A' in the periodontal pocket 32 and another position 'B' in the periodontal pocket 32. The position 'A' as a set point, is the intersection of an optical axis of the emitted beam of a first, optical axis FX and an optical axis of the reflected beam or second optical axis SX. The position 'B' is considered to be the bottom 32a of the periodontal pocket 32. The first optical axis FX and the second axis SX make an angle θ at the position 'A'. The position 'A' is fixed relative to the bottom surface 5a of the head portion 5 since it depends on the position of the second lens 2 relative to the position of the first lens 1, both of which are fixedly mounted within the head portion 5.

Assuming that the beam is reflected at the position 'A', the resultant or reflected beam which is in the form of an irregular reflected ray is focused on a central point of the plate 12 which is located on the second axis SX. This central point can be derived from a weighted-average of brightness distribution method. If the position 'B' is in coincidence with-the bottom 32a of the periodontal pocket 32, the reflected beam is focused on a point located at a distance δ from the central point. This point can be similar to the above, obtained from a weighted-average of brightness distribution.

If the reference symbol 'd' denotes the distance between the central point of the plate 12 and the central point of the lens 2, the reference symbol 'D' denotes the distance between the position 'A' and the central point of the lens 2, a distance Δ can be represented by the formula: $\Delta = \delta \cdot D / (m \cdot D \cdot \sin \Theta - \delta \cdot \cos \Theta)$, where $m = d/D$. Since the distance 'e' between the measuring criteria or the bottom surface 5a of the head portion 5 and the position 'A' is given or known, the depth of the periodontal pocket 32 or the distance between the measuring criteria and the bottom 32a of the periodontal pocket 32 may be calculated by summing 'e' and 'Δ'.

Figure 7:
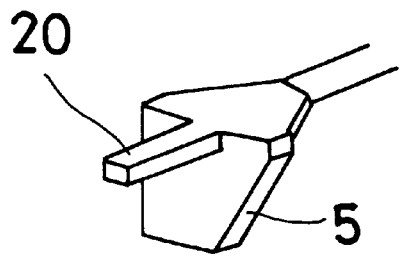
FIG. 7 is a perspective view of a first modification of the head portion.
Figure 8:
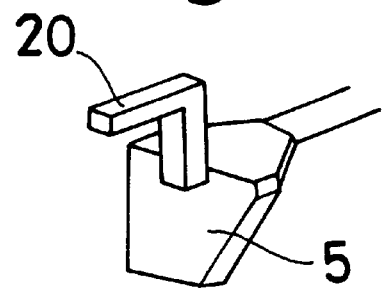
FIG. 8 is a perspective view of a second modification of the head portion.

In order to establish a more stable holding of the head portion 5, as shown in FIG. 7 (FIG. 8), the head portion 5 can be provided with a bar shaped projection 20 (an L-shaped projection 20) which is to be engaged with the top of the tooth 31. In addition, the bottom surface 5a as the measuring criteria can be brought into coincidence with the boundary of the enamel portion (not shown) on the tooth 31 instead of the gum line.

Figure 10:
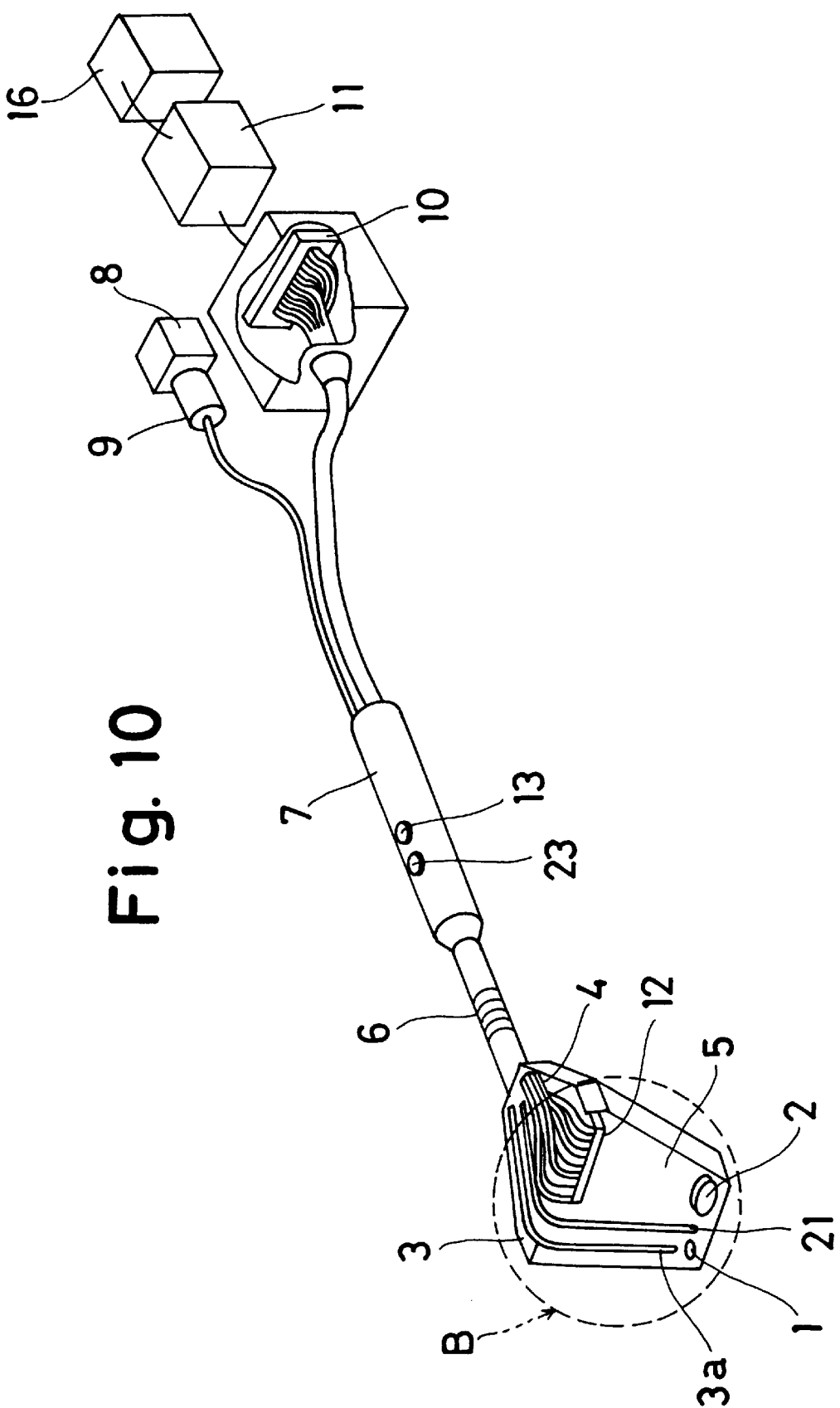
FIG. 10 is a diagram of a modification of the probe shown in FIG. 1.
Figure 11:
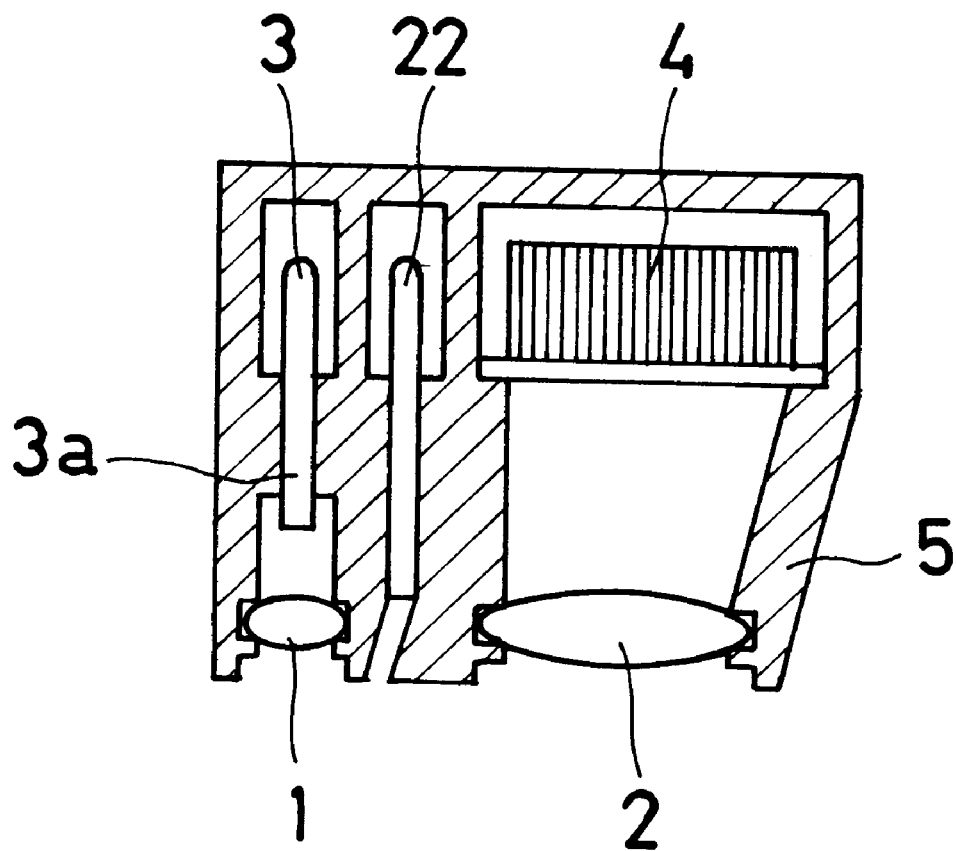
FIG. 11 is an enlarged cross-sectional view of portion B in FIG. 10.

As shown in FIGS. 10 and 11, an air nozzle 21 is extended into the head portion 5 and extends to next to the distal end portion 3a of the optical fiber 3. The air nozzle 21 is set to eject an air under pressure when a switch 23 is turned on, and the resultant air serves for expanding the opening of the periodontal pocket 32 or eliminating saliva within the periodontal pocket 32. The air nozzle can be designed so as to operate immediately upon closure of the switch 13, without providing the switch 23.

Figure 12:
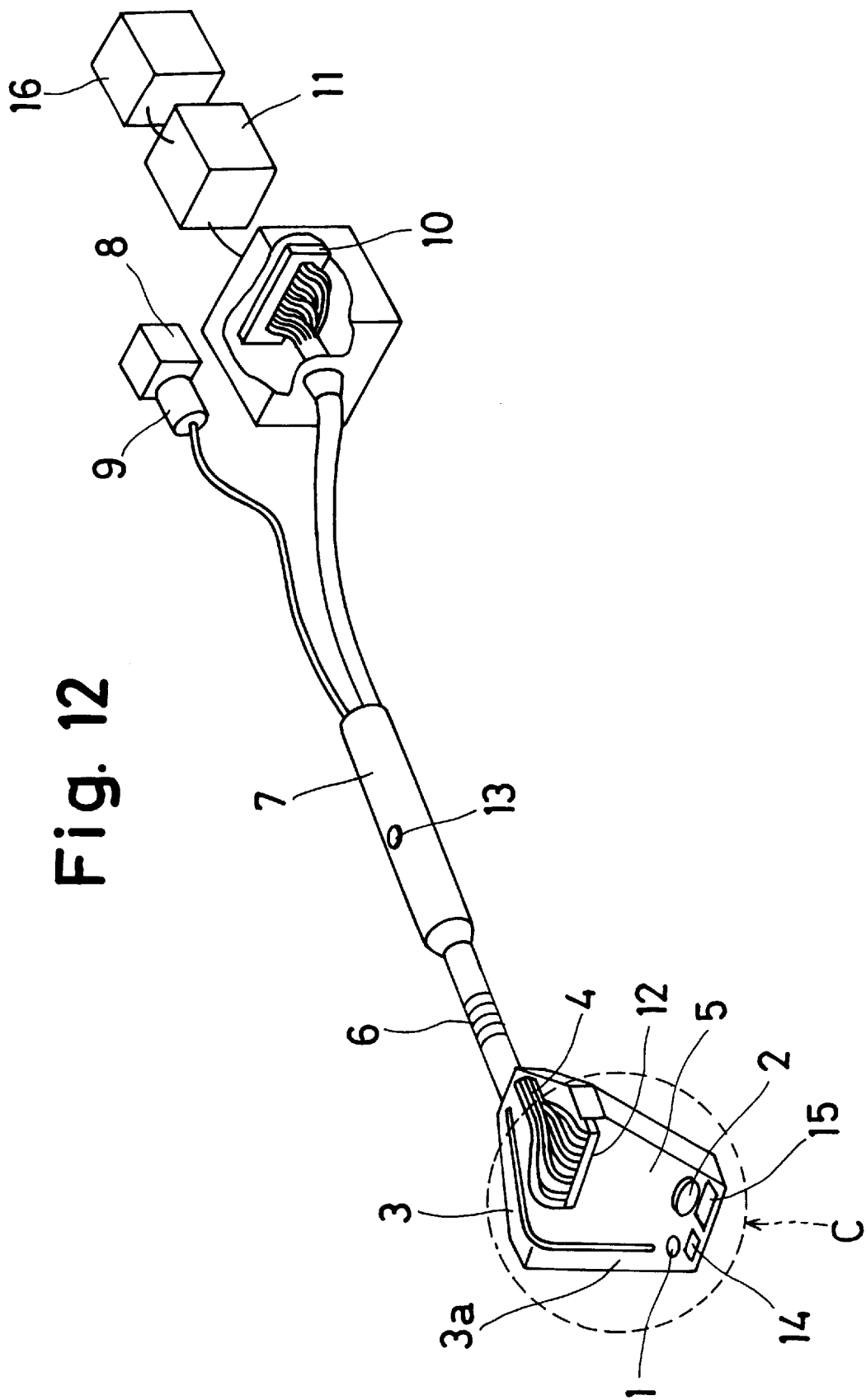
FIG. 12 is a diagram of another modification of the probe shown in FIG. 1.
Figure 13:
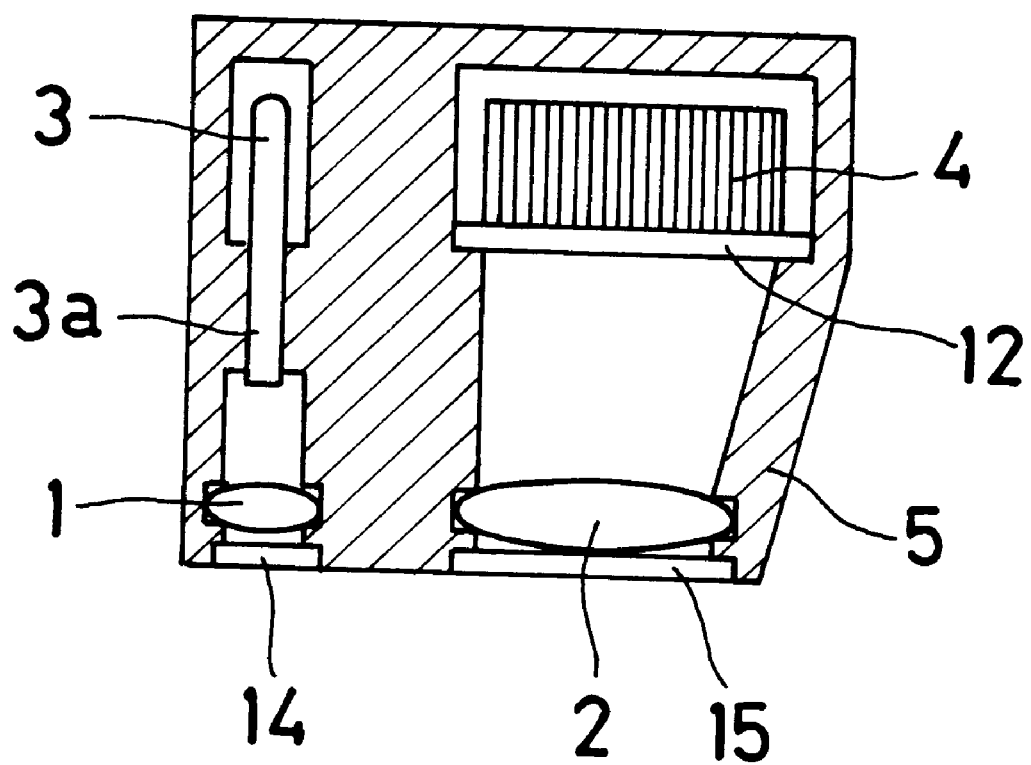
FIG. 13 is an enlarged cross-sectional view of portion C in FIG. 12.

As shown in FIGS. 12 and 13, a first polarizing plate 14 and a second polarizing plate 15 are provided close to the first lens 1 and the second lens 2, respectively. The laser beam which provides a small spot on the bottom 32a of the periodontal pocket 32 is non-polarized and becomes polarized after passing through the first polarizing plate 14. The polarization axes of the first polarizing plate 14 and the second polarizing plate 15 are crossed at right angles. When a saliva is adhered inside the periodontal pocket 32, the emitted beam toward the bottom 32a thereof is reflected by the saliva and the resultant beam is not a diffuse reflection beam which can pass through the second polarizing plate 15. Contrary to this, when the emitted beam makes a diffuse reflection the resultant beam can pass through the second polarizing plate 15. Thus, despite the adherence of saliva inside the periodontal pocket 32, a correct or precise calculation of the depth of the periodontal pocket 32 can be established.

In detail, as previously mentioned, in the calculation of the depth of the periodontal pocket 32, the central position of the plate 12 on the second optical axis and the position at a distance δ from central position of the plate 12 are calculated from the weighted average of the brightness distribution. If much saliva is adhered inside the periodontal pocket 32, both the reflected beam from the saliva and the reflected beam from the surface, per se, of the periodontal pocket 32 are used in the calculation of the weighted average of the brightness distribution, resulting in that an error occurs in such a calculation. However, employing a pair of the polarizing plates 14 and 15 whose polarizing axes are crossed at right angles eliminates the reflected beam from the saliva during the calculation of the weighted average of the brightness distribution, which permits a correct or precise calculation of the depth of the periodontal pocket 32.

Second Embodiment

Figure 14:
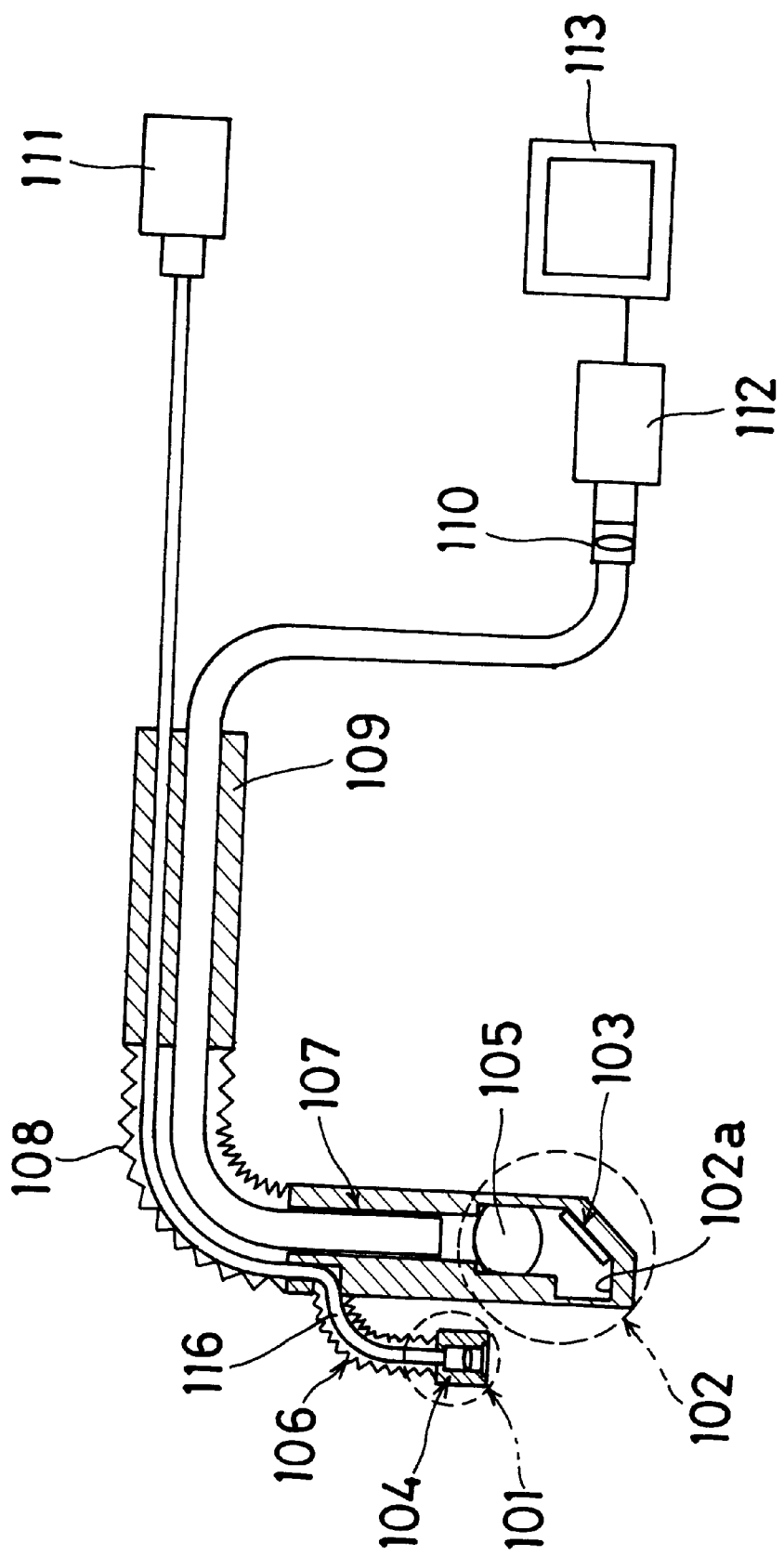
FIG. 14 is a diagram of a second embodiment of a probe according to the present invention.

Referring to FIG. 14, there is illustrated a second embodiment of a probe for measuring the depth of a periodontal pocket according to the present invention. The probe includes a handle portion 109 whose left end portion is connected to a light receiving portion 102 via a flexible tube 108 in the form of a goose neck. At a lower end portion of the light receiving portion 102, there is formed an opening 102a. Within the light receiving portion 102, there is accommodated a mirror 103 at an angle of about 45 degrees relative to the opening 102a. Above the mirror 103, a lens 105 is fixedly mounted in the light receiving portion 102. As the lens 105, a telecentric type is preferable. A left end portion of an optical fiber 107 which passes through the handle portion 109 and the flexible tube 108 is extended in the light receiving portion 102 and is opposed to the lens 105. Light from the mirror 102 is picked up by a CCD camera 112 after passing through the optical fiber 107 and an ocular 110. The resultant image is displayed on a visual display or CRT 113.

A light emitting portion 101 is provided at a distal end portion of a flexible tube 106 which is in the form of a goose neck. The flexible tube 106 is branched from an upper or proximal end portion of the light receiving portion 102. In the light emitting portion 101, a lens 104 is closely opposed to a left end portion of an optical fiber 116 which passes through the flexible tube 108 and the handle portion 109. A right end portion of the optical fiber 116 receives a laser beam from a laser emitting device or a light source 111, and a laser beam emitted from the light source 111 is projected from the light emitting portion 101 after being transmitted through the optical fiber 116 and the lens 104.

Figure 15:
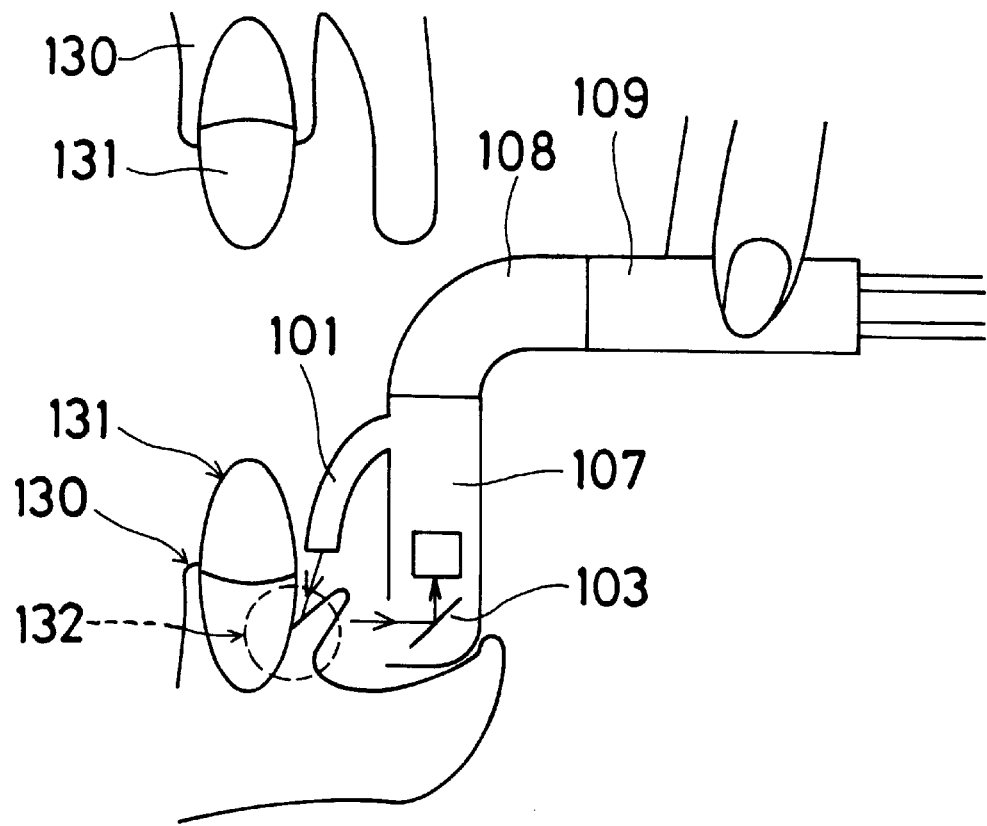
FIG. 15 is a view showing how the probe shown in FIG. 14 is used.
Figure 16:
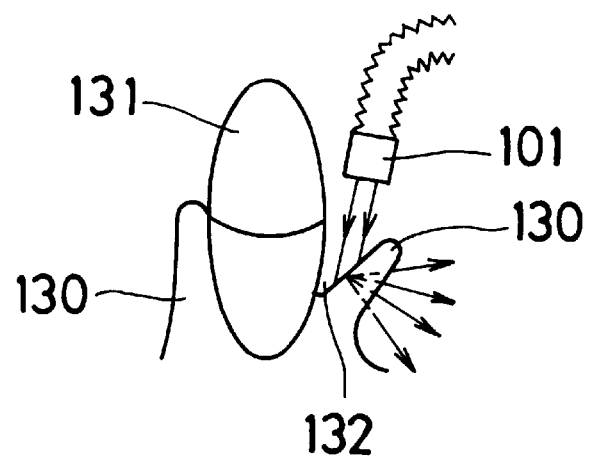
FIG. 16 shows the operation principle of the probe shown in FIG. 14.
Figure 17:
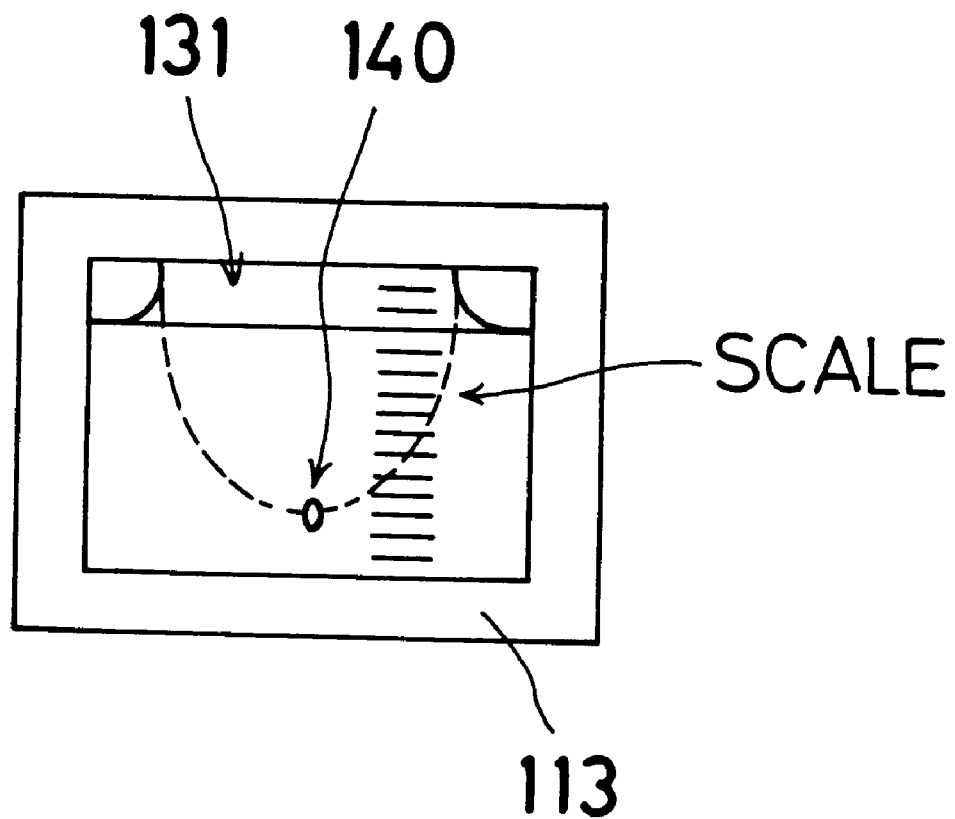
FIG. 17 is a view of the depth of the periodontal pocket measured by the probe shown in FIG. 14.

In operation, as shown in FIG. 15, the handle portion 109 is first manually held tightly in such a manner that the opening 102a of the light receiving portion 102 and the light emitting portion 101 are oriented to or aimed at, respectively, an outer periphery of a gum 130 and a periodontal pocket 132 formed between the gum 130 and a tooth 131. In this condition, no part of the probe is in contact with the periodontal pocket 132, a tooth 131, a gum 130 or another human part. Thereafter, when the light source 111 is turned on, the laser beam is projected toward the inside of the periodontal pocket 132 and passes through the gum 130 after being reflected inside the periodontal pocket 132 (FIG. 16). The resultant beam is transmitted by way of the mirror 103 and the optical fiber 107, and is picked up by the CCD camera 112, so that an inside condition of the periodontal pocket 132 may be displayed on the CRT 113 (FIG. 17) with a bottom of the periodontal pocket 132 being indicated by a laser spot 140. Since the CRT 113 is provided with a scale, the dimension of the periodontal pocket 132 can be seen. It is to be noted that the dimension of the periodontal pocket 132 on the CRT 113 can remain unchanged even though the light receiving portion 102 moves relative to the gum 130.

Figure 18:
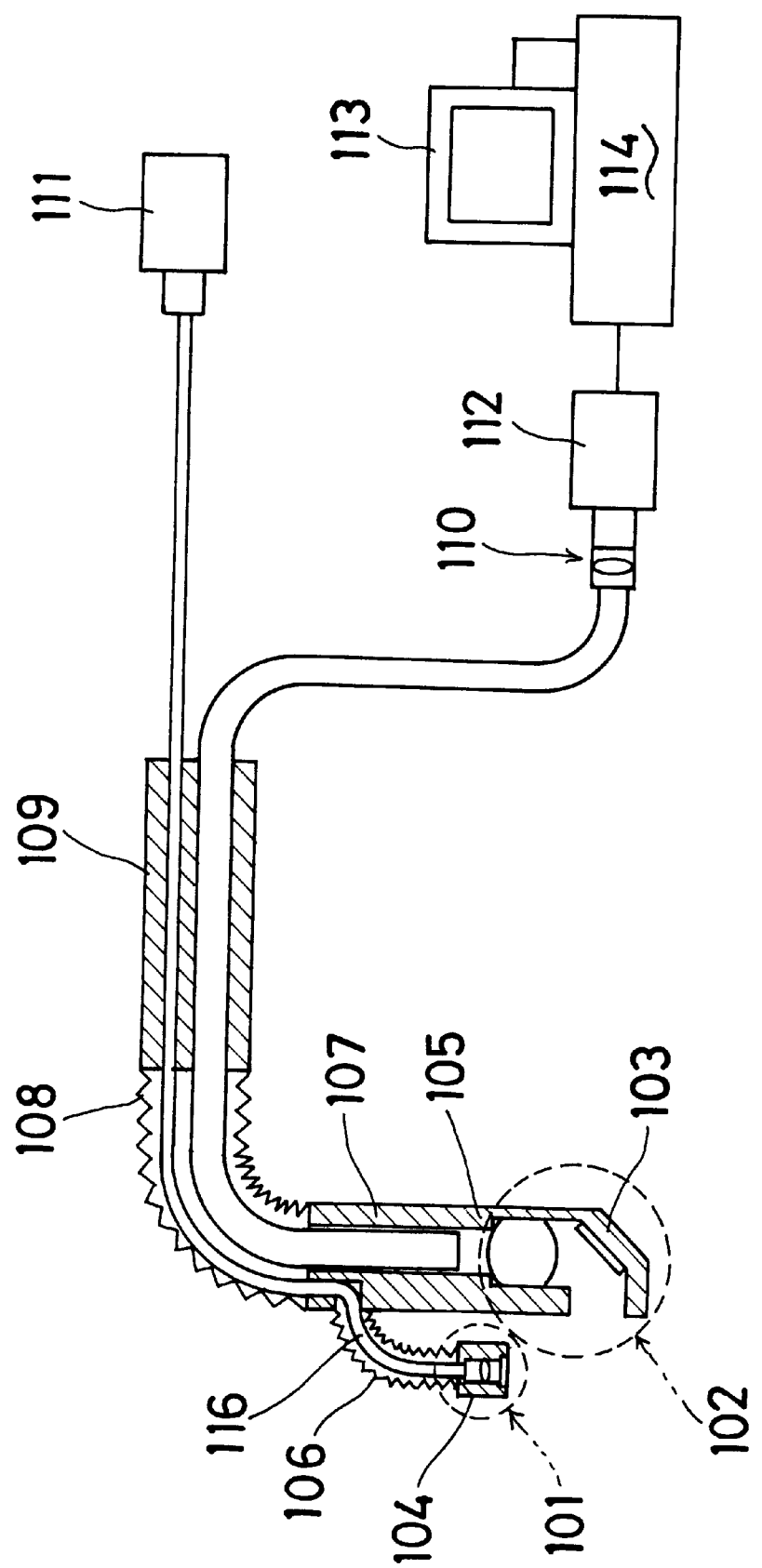
FIG. 18 shows a modification of the probe shown in FIG. 14.
Figure 19:
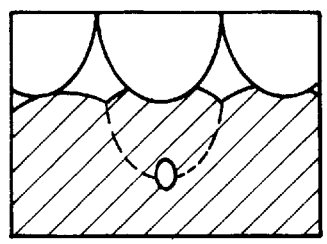
FIG. 19 is a view showing a picked-up image of a periodontal pocket.
Figure 20:
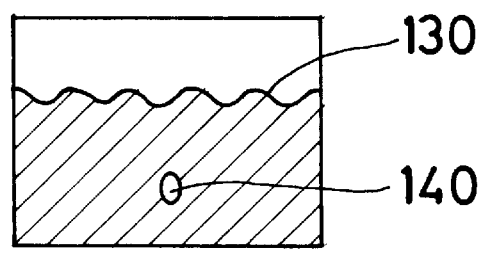
FIG. 20 shows a binary processed image of a periodontal pocket.
Figure 21:
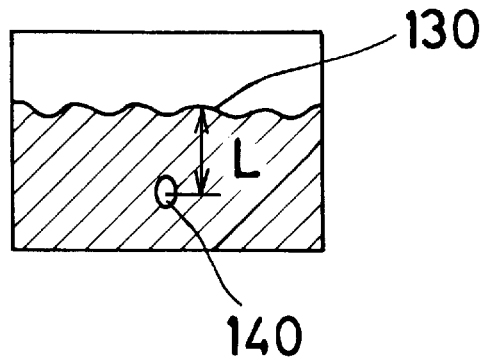
FIG. 21 shows how the depth of the periodontal pocket measured by the probe shown in FIG. 14 is displayed.

In FIG. 18, there is illustrated a modification of the probe shown in FIG. 14. In this device, instead of the foregoing scaled CRT 113, a display or CRT 113A is in association with an image processor 114. In this device, the image of the periodontal pocket 132 is picked-up by the CCD camera 112. The picked-up image of the periodontal pocket 132 as shown in FIG. 19 is formed into a binary processed image as shown in FIG. 20 by the image processor 114. On the basis of such a binary processed image, a center of gravity of the laser spot 140 is calculated, which indicates the bottom of the periodontal pocket 132. A length L between the resultant center of gravity and a top of the gum 130 or the depth of the periodontal pocket 132 is determined and displayed on the CRT 113A as shown in FIG. 21.

Third Embodiment

Figure 22:
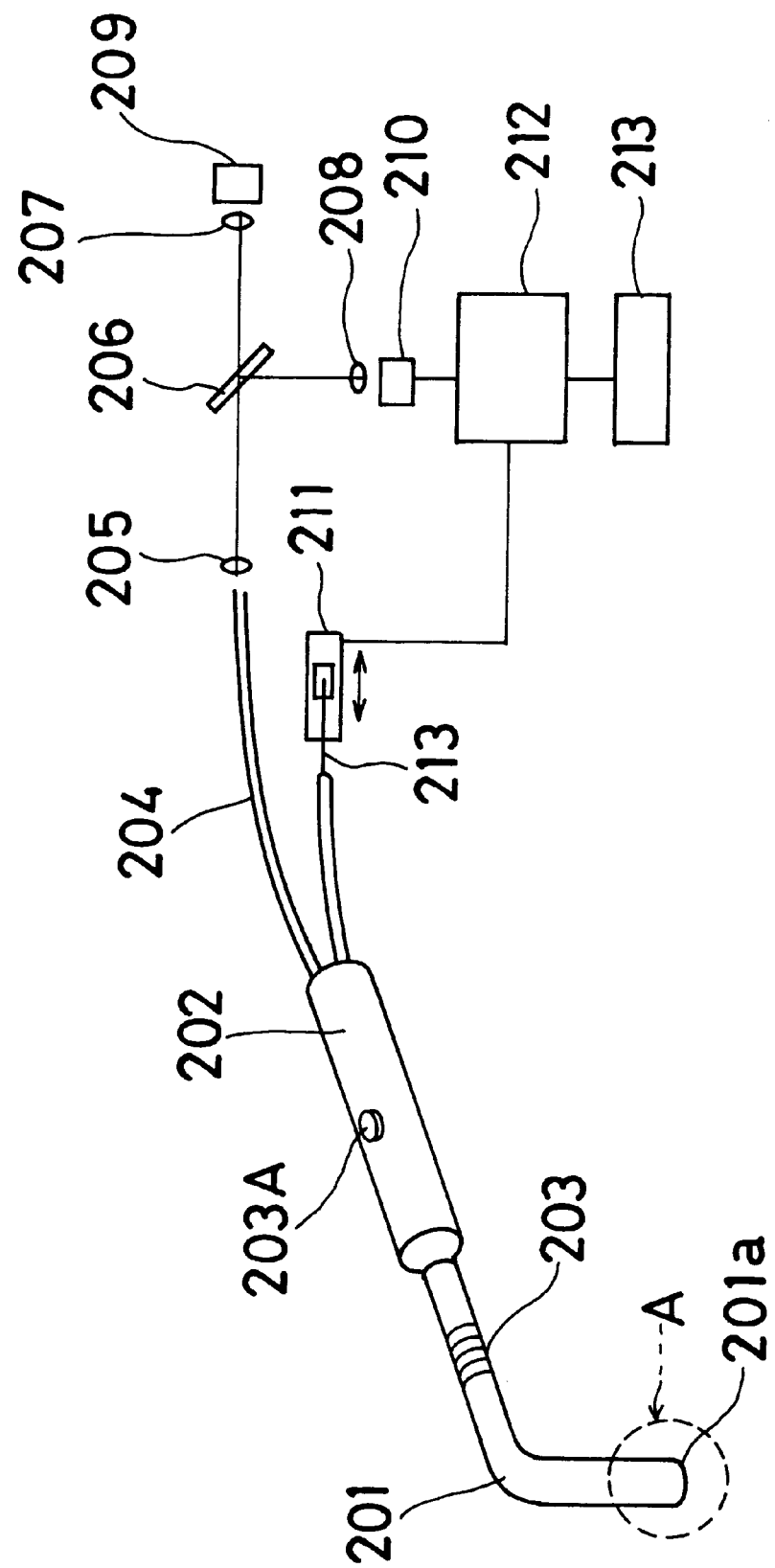
FIG. 22 is a diagram of a third embodiment of a probe according to a third embodiment of the present invention.
Figure 23:
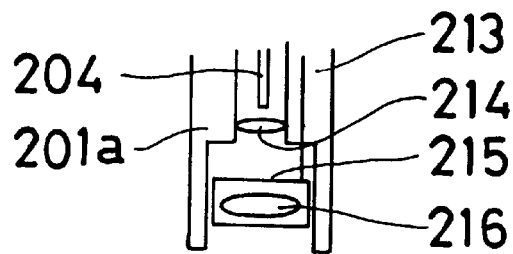
FIG. 23 is an enlarged cross-sectional view of portion A in FIG. 22.
Figure 24:
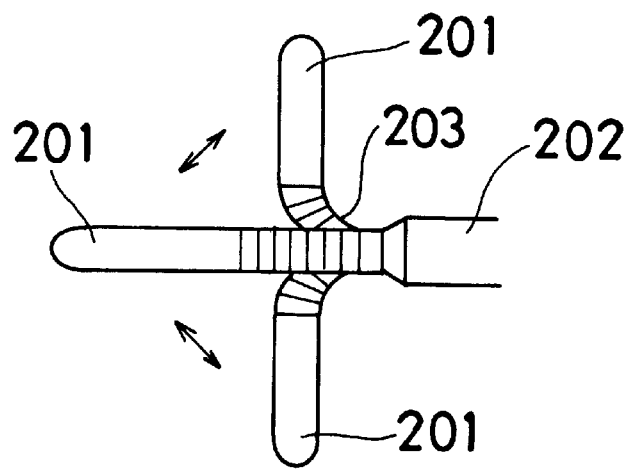
FIG. 24 shows movements of the probe shown in FIG. 22.
Figure 25:
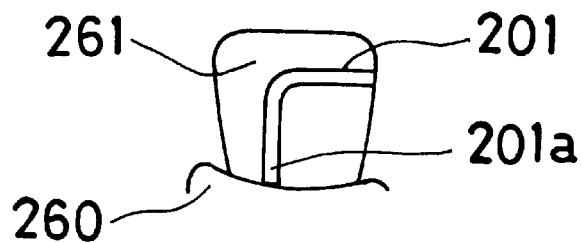
FIG. 25 is a side view showing how the probe shown in FIG. 22 is used.
Figure 26:
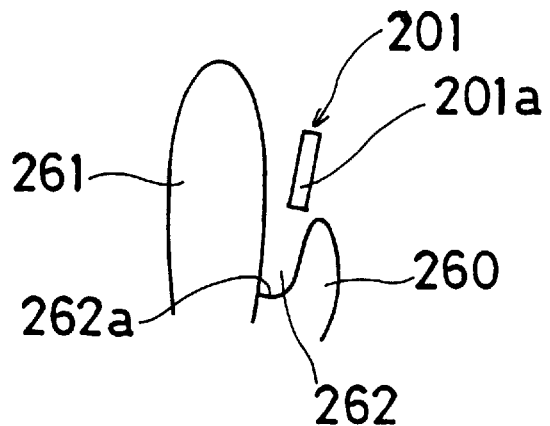
FIG. 26 is a cross-sectional view showing the probe shown in FIG. 22 being used.

Referring to FIGS. 22 through 26, there is illustrated a probe 201 which is designed for measuring the depth of the periodontal pocket 262. A right end or proximal portion of the probe 201 is connected to a handle portion 202. A portion of the probe 202 is formed into a flexible configuration 203 so as to be movable in any direction relative to the handle portion 202, as best shown in FIG. 24. A distal or left end portion of an optical fiber 204 which passes through the handle portion 202 is extended into the probe 201 and is fixedly mounted therein so as to be in close opposition to a lens 214 which is located at a position slightly away from an open distal or left end portion 201a of the probe 201.

Within the open distal end portion 201a of the probe 201, there is provided a holder 215 in which a further lens 216 is fixed. The holder 216 is connected to a wire 213. Pulling or pushing the wire 213 by controlling a driver 211 which will be detailed later moves the holder 215 in the axial direction. A proximal or right end portion of the optical fiber 204 is in opposition to a laser emitting device 209 as a light source via a lens 205, a half-silvered or semi-transparent mirror 206 and a lens 207.

A laser beam emitted from the device 209 is formed into a parallel light after passing through the lens 207. The resultant beam passes through the lens 205 and converges at a focal point thereof near the right end portion of the optical fiber 204.

Then, the beam is transmitted through the optical fiber 204 and is projected from the left or distal end portion thereof to the lens 214.

Thereafter, the beam is projected through the lens 216 onto a bottom 262a of the periodontal pocket 262 formed between a tooth 261 and a gum 260 (FIG. 26) in such a manner that the projected beam makes a spot on the bottom. The resultant diffuse reflected beam is collumnated by the lens 205 after being guided by the optical fiber 204 and is guided to a lens 208 after being reflected by the semitransparent mirror 206. The light, after passing through the lens 208, is converted at an optical sensor 210 into an electric signal. This signal is fed to a data processing portion or controller 212.

The driver 211 is under the control of the controller 2130 which orders the driver 211 to pull or push the wire 213 together with the holder 215 which accommodates therein the lens 216 so that the maximum value of the electric signal can be obtained or detected.

In operation, the flexible portion 203 of the probe 201 is first bent in a suitable manner and the handle portion 202 is held in such a manner that the distal end portion of the probe 201 is coincided with a reference or criteria level such as a top of the gum 260 or a boundary of the enamel portion on the tooth 261, so as to be oriented to the bottom 262a of the periodontal pocket 262. In such a condition, no part of the probe 201 and the handle portion 202 is in contact with a human portion. When a switch 203A on the handle portion 202 is turned on, the laser beam emitted from the laser emitting device 209 is projected on the bottom of the periodontal pocket 262. If the beam focuses on the bottom of the periodontal pocket 262, the resultant diffuse reflection transmitted to the left end portion of the optical fiber 204 becomes maximum.

Figure 27:
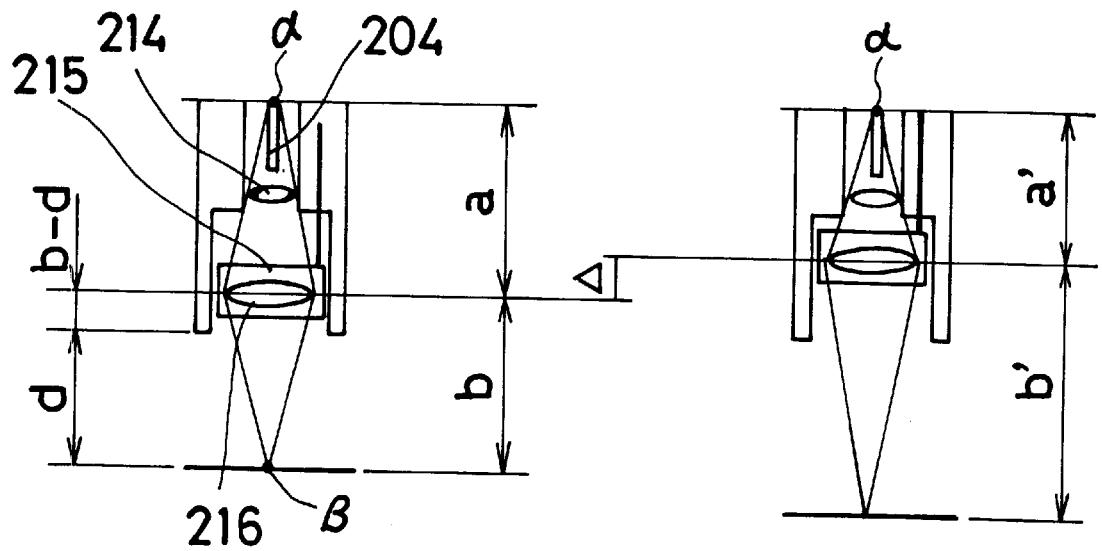
FIG. 27 shows how the depth of the periodontal pocket can be measured by using the probe shown in FIG. 22.

As shown in FIG. 27A, a distance 'd' is first determined so that point $\alpha$ and point $\beta$ are conjugate points and the sum of a distance [a] and a distance [b] constitute a conjugate distance. Thus, an original position of the holder 215 accommodating therein the lens 216 is determined. As shown in FIG. 27B, when the reflected beam transmitted to the left end portion of the optical fiber 204 becomes maximum at a position after the holder 215 moves a distance $\Delta$, a length [b'] can be represented by the formula: $b'=(a-\Delta)f/(a-\Delta-f)$, where f represents the focus length of the lens 216. Thus, the distance between the bottom of the periodontal pocket 262 and the distal end of the probe 201 which equals the depth of the periodontal pocket 262 can be represented by $b'-\Delta-b+d$.

Since $\Delta$ equals a travel or displacement of the wire 213, measuring such a displacement by an encoder (not shown) provided to the driver 211 establishes an easy determination of $\Delta$.

It is to be noted that such a calculation ignores an elasticity of the wire 213 and therefore some degree of error is inevitable in the calculation. To assure a more precise calculation, a correction has to be made by measuring a force for pushing or pulling the wire 213. In addition, a direct measurement of the displacement of the wire 213 can be established by accommodating a slide resistor or magnetic resistor in the probe 201, per se. It is to be noted that the calculated depth of the periodontal pocket 262 is displayed on a digital display 213.

Figure 28:
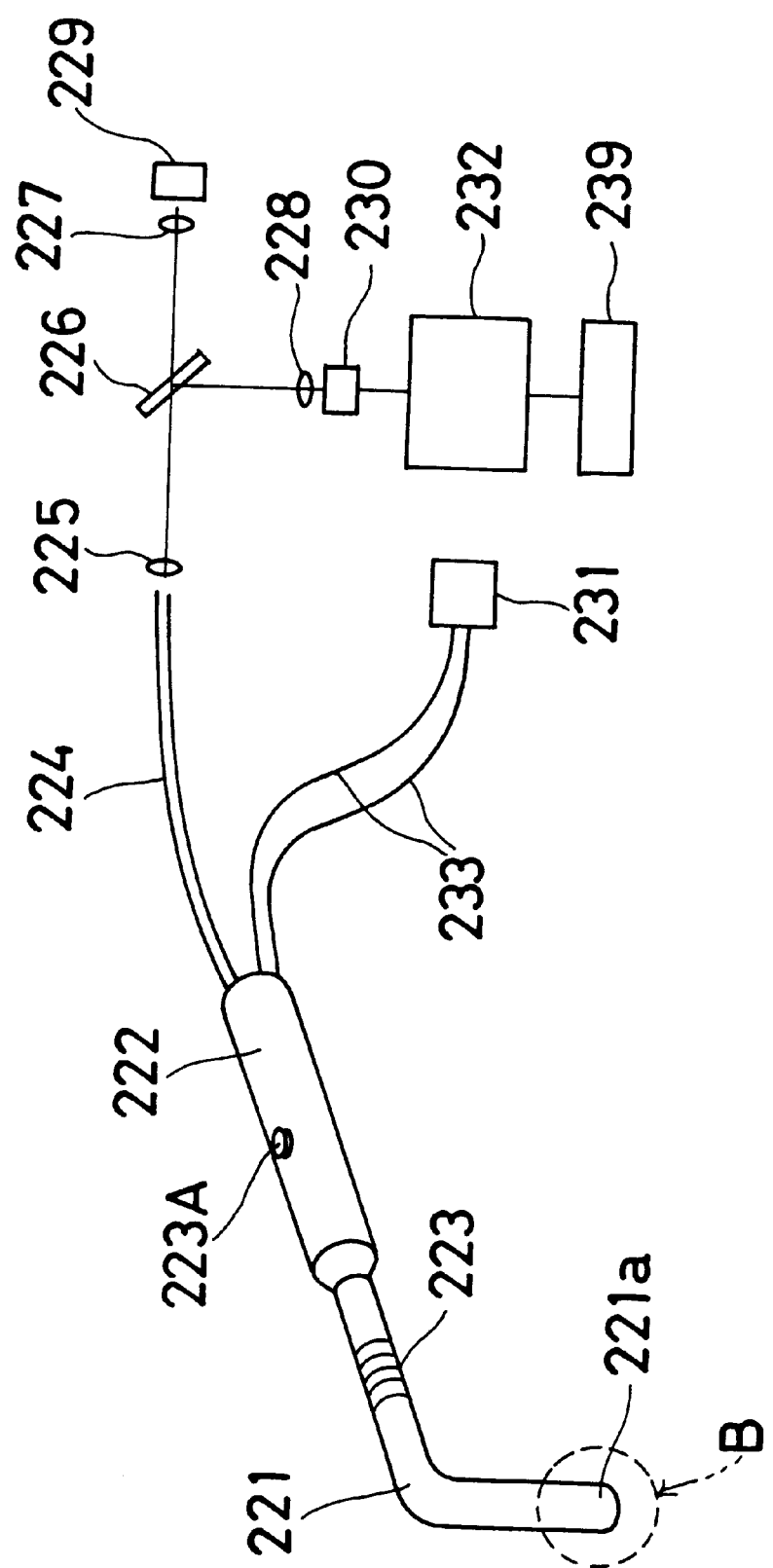
FIG. 28 is a diagram of a modification of the probe shown in FIG. 22.
Figure 29:
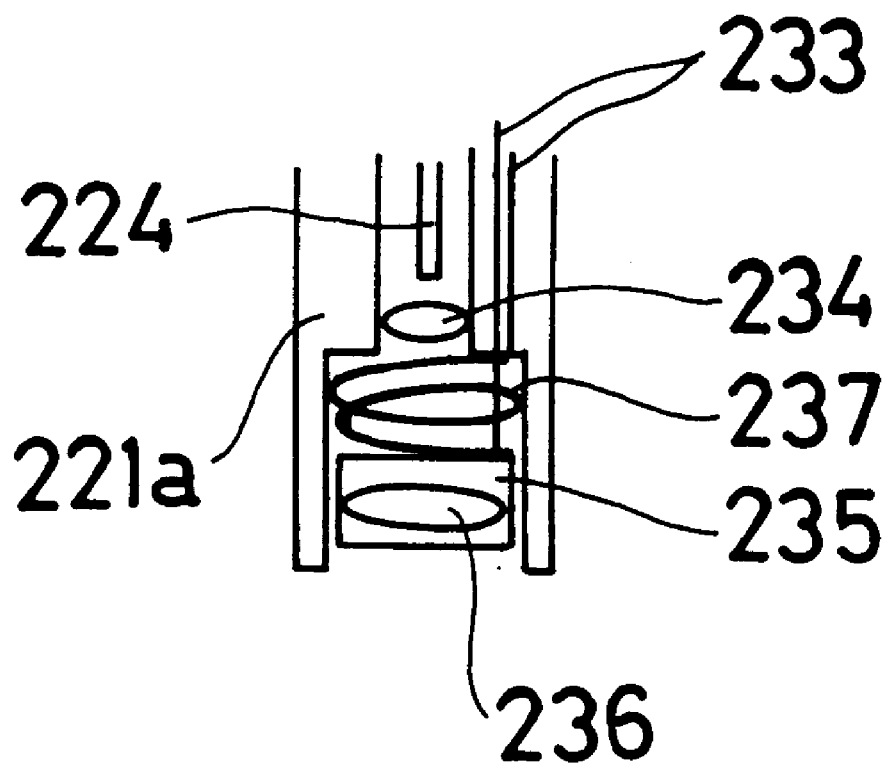
FIG. 29 is an enlarged cross-sectional view of portion B in FIG. 28.

Referring to FIGS. 28 and 29, there is illustrated a probe 221 which is similar to the aforementioned probe 201 except that in the latter a shape memory alloy 237 is used instead of the wire 213 in the former. In detail, a holder 235 in which a lens 236 is fixed is connected to the shape memory alloy 237 whose ends are connected to both terminals 233 of a power supply 23 1. The axial displacement of the holder 235 depends on the amount of supplied current to the shape memory alloy 237 from the power supply 231. Thus, when the maximum beam is obtained at the left end of the optical fiber 224 as a result of a specific displacement of the holder 235, the foregoing distance $\Delta$ can be derived from a measurement of the corresponding current supplied to the shape memory alloy 237 establishing such a displacement. For establishing more precise measurement, as in the probe 201, a direct detection of $\Delta$ is preferable by accommodating a slide resistor or magnetic resistor in the probe 201.

It is to be noted that reference numerals 221a, 222, 223A, 224, 225, 226, 227, 228, 229, 230, 232 234 and 239 denote respectively identical or equivalent elements 201a, 202, 203A, 204, 205, 206, 207, 208, 209, 210, 214 212, and 2130.

Figure 30:
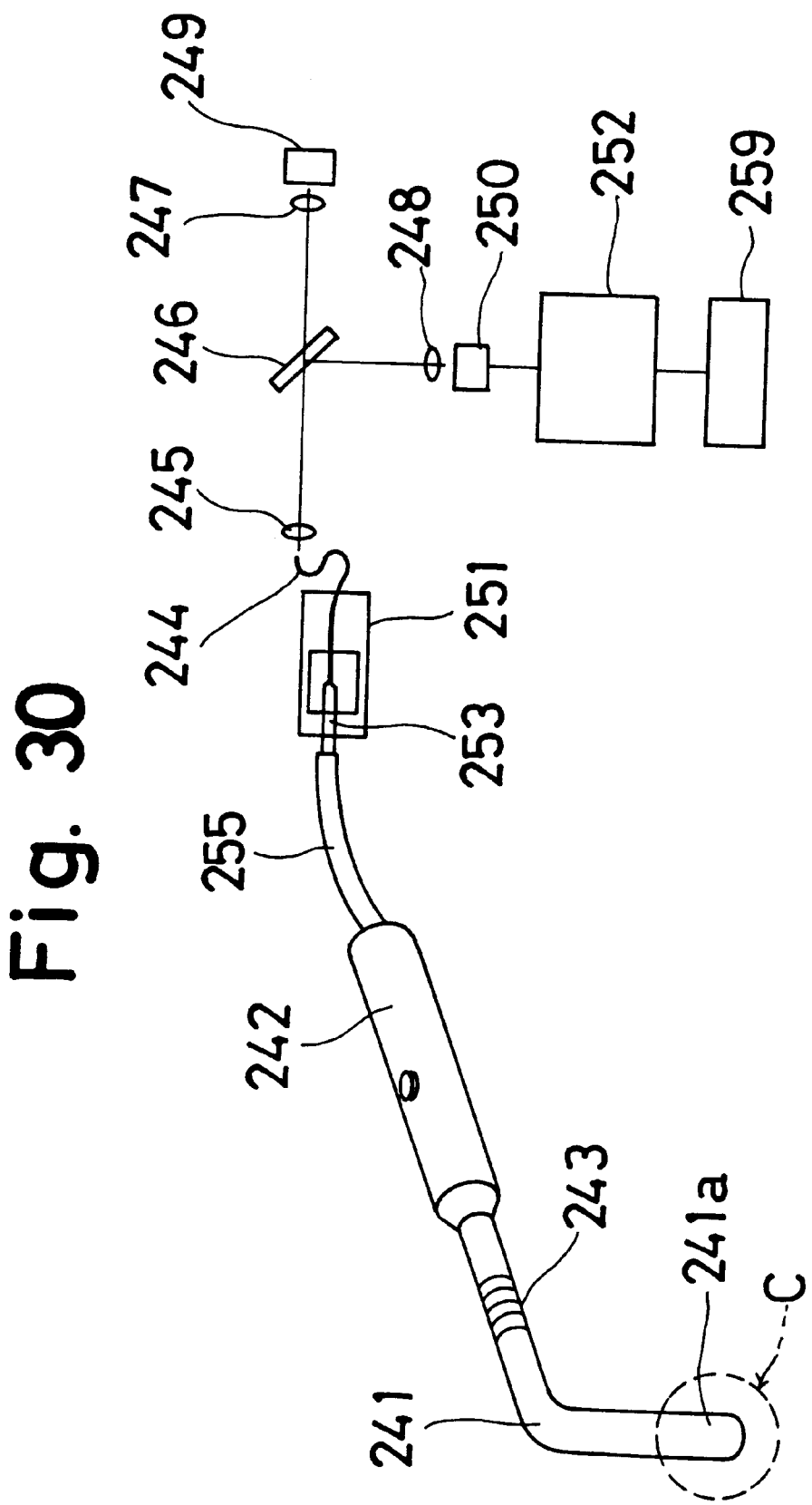
FIG. 30 is a diagram of another modification of the probe shown in FIG. 22.

Referring to FIGS. 30 through 32, there is depicted a probe 241 in the form of an L-shaped configuration and connected to a handle portion 242. The probe 241 is provided at its a part near the handle portion 242 with a flexible portion 243 so as to be movable or displaceable in any direction relative to the handle portion 242. A pipe 255 passes through the handle portion 242 and is extended into the probe 241. Along the pipe 255, an optical fiber 244 surrounded by or covered with a protecting cover or tube 253 is extended and terminated in a portion near a lens 254 which is fixedly mounted in a distal end portion of the pipe 255. The tube 253 and the optical fiber 244 are set to be brought into unitary movement by a driver 251.

A right end portion of the optical fiber 244 receives a laser beam from a laser emitting device 249 as a light source via a lens 247, a semi-transparent mirror or halfsilvered mirror 246 and a lens 245. The laser beam emitted from the device 249 is collumnated after passing through the lens 247. The resultant beam passes through the semi-transparent mirror 246 and the lens 245, and converges at a focal point near the right end portion of the optical fiber 244. Then the beam is transmitted by the optical fiber 244 and is projected from the left or distal end portion thereof to the lens 254.

Thereafter, the beam is projected through the lens 254 onto a bottom of the periodontal pocket (not shown) in such a manner that the projected beam makes a spot on the bottom. The resultant diffuse reflected beam is collumnated by the lens 245 after being guided by the optical fiber 244 and such a parallel light is guided to a lens 248 after being reflected by the semi-transparent mirror 246. The light is, after passing through the lens 248, converted into an electric signal at an optical sensor 250. The resultant electric signal is fed or transmitted to a data processing portion or controller 252.

The driver 251 is under the control of the controller 259 which orders the driver 251 to pull or push the tube 253 accommodating therein the lens 254 so that the maximum value of the electric signal can be obtained or detected.

The operation principle of the probe 241 is similar to that of the probe 201 and can be used to determine the depth of the periodontal pocket, which is defined as the difference between the distal end 241a of the probe 241 and the bottom of the periodontal pocket, as the sum of d and $\Delta$, as shown in FIGS. 32A and 32B.

Figure 33:
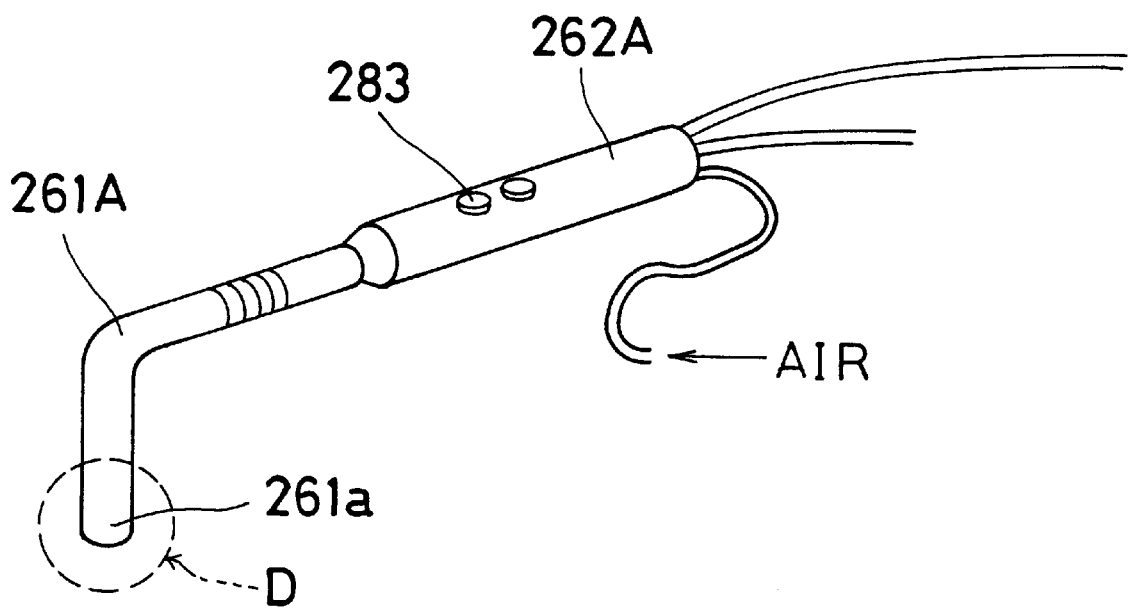
FIG. 33 is a diagram of a third modification of the probe shown in FIG. 22.
Figure 34:
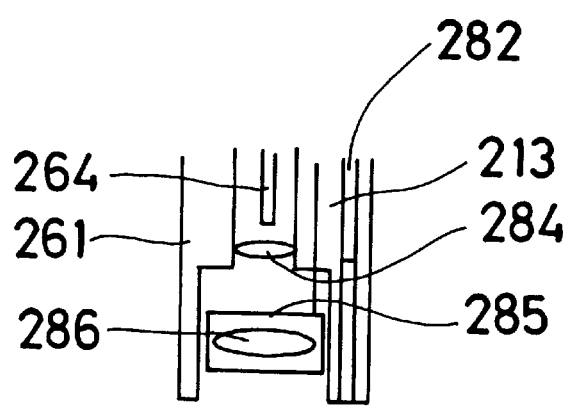
FIG. 34 is an enlarged cross-sectional view of portion D in FIG. 33.

FIGS. 33 and 34 show a probe 261A which is similar to the probe 201 shown in FIG. 22 except that an air nozzle 282 is provided. Such an air nozzle 282 extends into the probe 261A and terminates at a position near a distal end portion 261a of the probe 261. When a switch 283 provided on a handle portion 262A is turned on, air under pressure is ejected from a distal end portion of the nozzle 282 toward a periodontal pocket. Such an ejection serves for expanding an opening of the periodontal pocket and/or eliminating saliva for easy measurement of the depth of the periodontal pocket.

Elements 285 and 286 correspond to elements 215 and 216 of FIG. 23, respectively.

Fourth Embodiment

Figure 35:
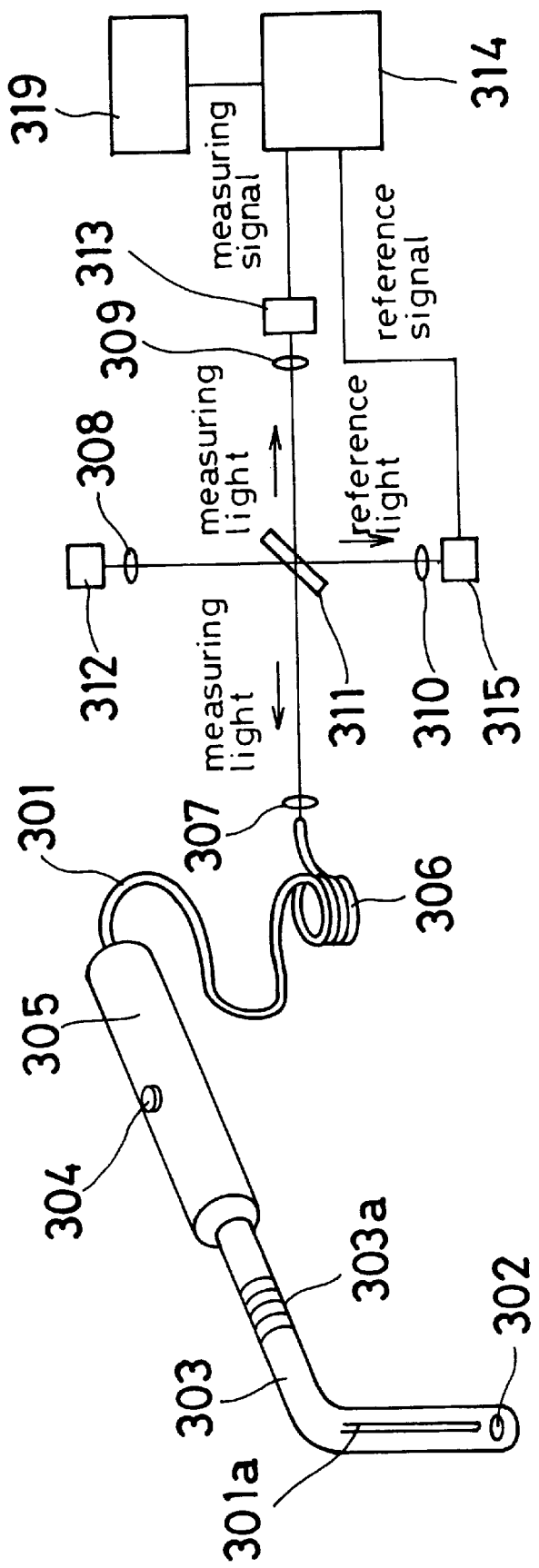
FIG. 35 is a diagram of a fourth embodiment of a probe according to the present invention.
Figure 36:
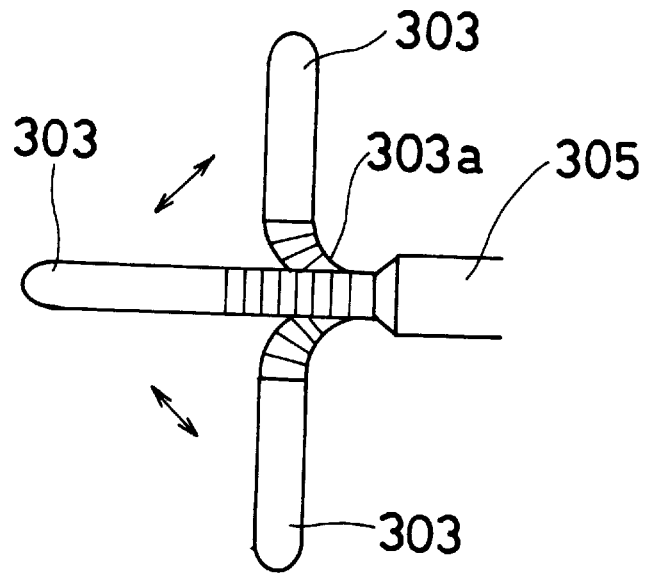
FIG. 36 shows movements of a head portion of the probe shown in FIG. 35.

Referring to FIGS. 35 and 36, a periodontal probe device includes a handle portion 305 and is connected at its left end portion with an L-shaped probe 303. A portion of the probe 303 near the handle portion 305 is formed into a flexible configuration 303a so as to be movable in any direction relative to the handle portion 305 as shown in FIG. 36. An optical fiber 301 is extended from a light delay circuit 306 which serves for forming a suitable optical path length and is extended into the handle portion 305 and the probe 303.

A distal or left end portion 30 1a of the optical fiber 301 is in close opposition to a lens 302 which is fixedly mounted to a distal or left end portion of the probe 303.

A proximal or right end portion of the light delay circuit 306 is in close opposition to a lens 307 which is spaced from a lens 309 on a common principal or optical axis. Between the lens 307 and the lens 309, a semi-transparent mirror 311 as a beam splitter is disposed so as to make an angle of 45 degrees relative to the common principal axis. The semi-transparent mirror 311 is also disposed on another principal axis on which a set of spaced lenses 308 and 310 are disposed. Both principal axes meet at right angles and on the resultant point a center of the semi-transparent mirror 311 is located.

The semi-transparent mirror 311 is in opposition to a laser beam emitting device 312 (an optical sensor 315) via the lens 308 (the lens 310). A laser beam emitted from the device 312 is first collumnated by the lens 308 and is transmitted to the semi-transparent mirror or beam splitter 311. Then the light is divided at the beam splitter 311 into two parts: one, after reflection thereon, travels toward the lens 307 as a measuring light and the other, after passing through the splitter 311, travels toward the lens 310 as a reference or criteria light.

The measuring light is projected from the distal end portion 301a of the optical fiber 301 toward a bottom of a periodontal pocket 332 after passing through the lens 307 and the light delay circuit 306. The projected light is reflected on the bottom of the periodontal pocket 332 and the resultant light is transmitted to an optical sensor 313 after passing through the optical fiber 301, the light delay circuit 306, the beam-splitter 311, and the lens 309. The light is converted into a measuring electric signal at the optical sensor 313 and the resultant signal is fed to the controller 314. On the other hand, the reference light is fed to the optical sensor 315 after passing through the lens 310 and is converted into a reference electric signal at the optical sensor 315. The resultant signal is fed to the controller 314 and both electric signals are compared each other as will be detailed later.

Figure 37:
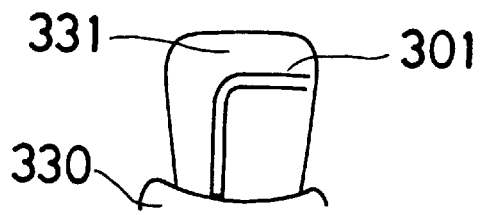
FIG. 37 is a side view showing how the probe shown in FIG. 35 is used.
Figure 38:
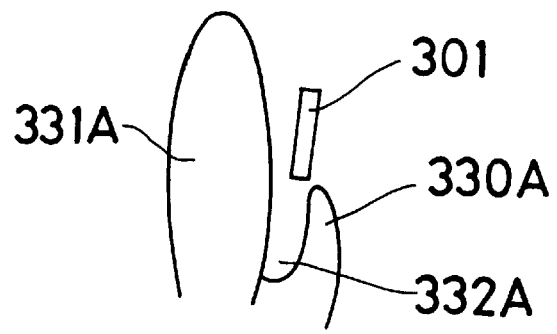
FIG. 38 is a cross-sectional view showing the probe shown in FIG. 35 being used.
Figure 39:
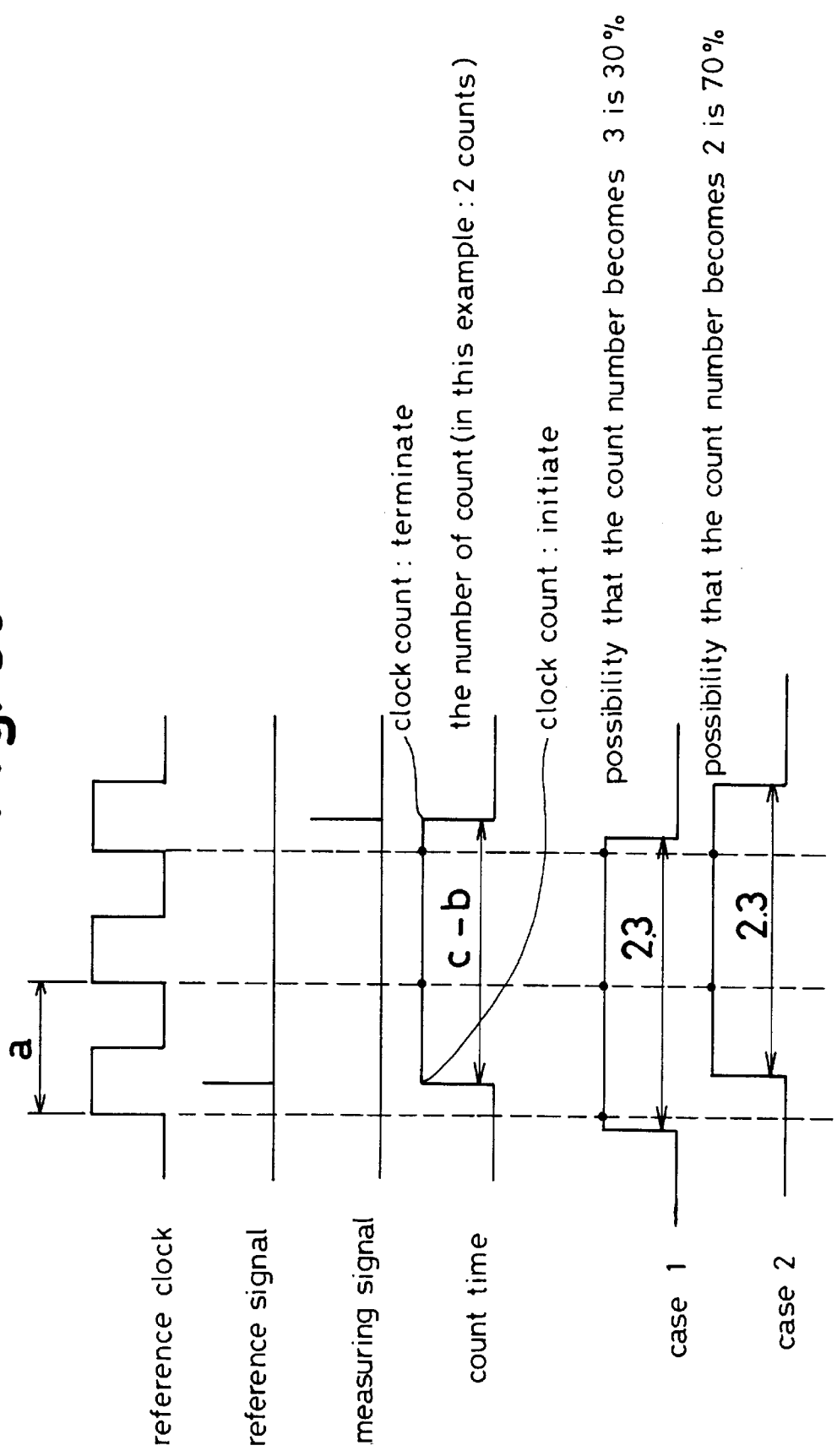
FIG. 39 shows how a depth of the periodontal pocket can be measured by using the probe shown in FIG. 38.

Hereinafter, with reference to FIGS. 37 through 39, how the depth of the periodontal pocket 332A is measured by the probe 303 will be described. First the handle portion 305 is fixedly held such that the distal end portion of the probe 302 is oriented to or aimed at the bottom of the periodontal pocket 332A between the tooth 331A and the gum 330A. Then, a switch 304 on the handle portion 305 is turned on and a reference or criteria clock within the controller 314 generates a pulse signal having a duration 'a'. The count of the reference clock is initiated immediately when a pulse of the reference signal is raised and is terminated immediately when a pulse of the measuring signal is lowered. When the count of the reference clock is k, an optical path of the reference light is defined as b and an optical path of the measuring light is defined as c, the differential optical path (c−b) can be represented as a formula of $(c-b) = k \cdot a$.

If a distance between the laser emitting device 312 and the distal end portion 301a of the optical fiber 301 is defined as d, and a distance between the optical sensor 313 and the distal end portion 301a of the optical fiber 301 is defined as e, a distance x between the distal end portion 301a of the optical fiber 301 and the bottom of the periodontal pocket 332A can be obtained by a formula: $x = \{(c-b) - d - e\}/2 = (k \cdot a - d - e)/2$. Since [d] and [e] are given and [a] can be obtained by using the frequency of the reference clock and the speed of light, the depth of the periodontal pocket 332A can be determined or calculated.

The resultant or calculated depth of the pocket 332A is displayed on a display or CRT 319.

The value [a] also can be obtained by measuring and/or modifying a previously prepared or sample reference clock.

If a pulse length of the reference clock is not adequate for measuring the depth x of the periodontal pocket, calculating an average of the plural measured depths x may be done after establishing more than one shot of the reference dock between the reference signal and the measuring signal, resulting in a measurement of the depth of the periodontal pocket regardless of the resolving power or resolution of the device.

If the depth x of the periodontal pocket 232A corresponds to a time duration between the rises of the reference signal and the measuring signal which is measured by 2.3 shots of the reference clock, setting a random rise of the pulse of the reference signal relative to the reference clock, the possibility that the number k becomes 2 (3) is 70% (30%). Thus, increasing the number of measurements enables the average of the measured value to approach the actual value according to the probability theory.

Figure 40:
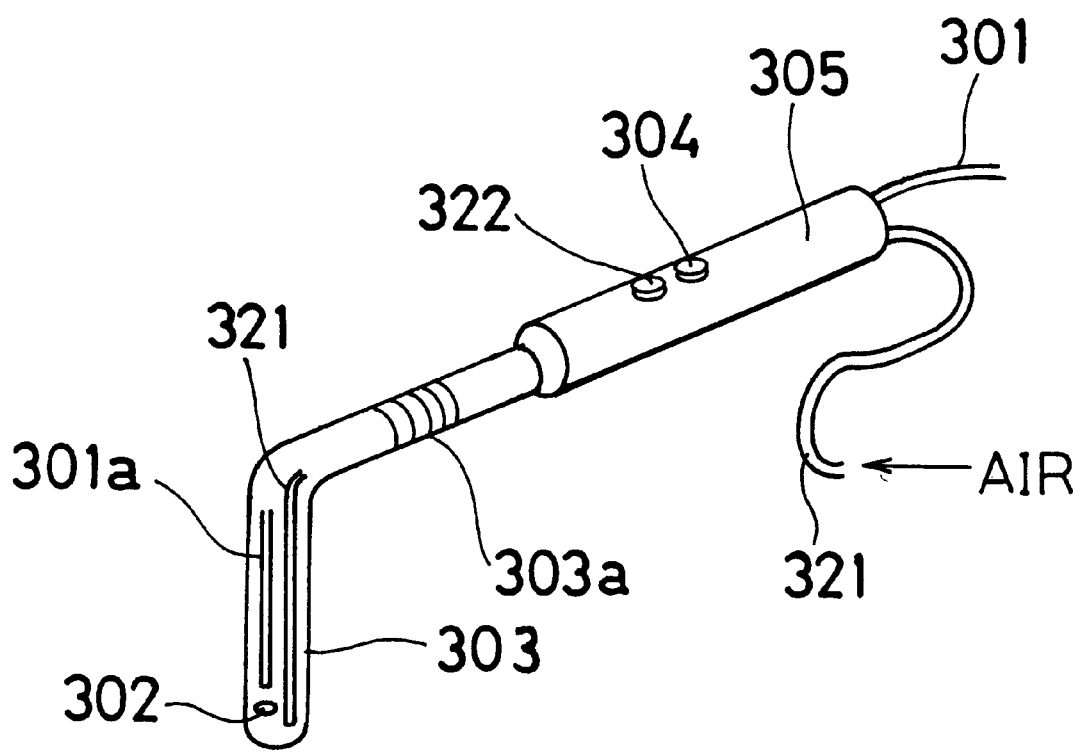
FIG. 40 is a diagram of a modification of the probe shown in FIG. 35.

It is to be noted that, as shown in FIG. 40, an air nozzle 321 may be provided in the probe 303.

Referring to FIGS. 40 and 41, there is illustrated a probe device which is a modification of the probe device shown in FIG. 35. Compared to the former, the latter is the same except that a travel direction of a reference light is inverted at an inverter 338 and the resultant light is transmitted to a lens 334. The inverter 338 is fixed within a holder 339 which is moved upon receipt of a signal from a controller 340, and no element is provided which is identical with or equivalent to the light delay circuit 306 of the former. It also has an air nozzle 321 operated by switch 322.

In the controller 340, an original position of the holder 339 is stored and the reference signal is combined with the measuring signal. At a position of the holder 339 during its movement, if a phase of the reference signal is coincident with a phase of the measuring signal, the amplitude of the combined signal takes its peak or maximum value. Thus, the distance between a position at which the resultant peak value is established and the original position is a displacement of the holder 339 which denotes the depth of the periodontal pocket.

Elements 333,335,336,337 and 341 correspond to elements 309, 315,312,313 and 319 of FIG. 35.

The invention has thus been shown and described with reference to a specific embodiment, however, it should be noted that the invention is in no way limited to the details of the illustrated structures but changes and modifications may be made without departing from the scope of the appended claims.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A probe for measuring a depth of a periodontal pocket, comprising:

emitting means for emitting a light beam from a position at a distance from the periodontal pocket toward the periodontal pocket so that the light beam may be reflected on a bottom of the periodontal pocket;

receiving means at a position at another distance from the periodontal pocket for receiving the reflected light beam; and analyzing means for determining the depth of the periodontal pocket on the basis of the light beam received at the receiving means, wherein said analyzing means includes means for determining the depth of the periodontal pocket by triangulation.

2. A probe as set forth in claim 1, wherein the reflected light beam is comprised of a diffuse reflected light, the analyzing means includes a CRT on which a scale is provided, and an image based on the determined depth of the periodontal pocket is displayed on the CRT with the bottom of the periodontal pocket indicated by the scale.

3. A probe as set forth in claim 1, including means for providing a maximum magnitude of the reflected beam detected by the receiving means by displacing a lens by a distance relative to the bottom of the periodontal pocket.

4. A probe as set forth in claim 1, including means for obtaining a reference signal and a measuring signal from the reflected beam, and means in the analyzing means for correlating the reference and measuring signals for calculating the depth of the periodontal pocket.

5. A probe for measuring the depth of a periodontal pocket comprising:

emitting means for emitting a beam;

a head portion positionable near the periodontal pocket;

a first lens located in the head portion and having a first optical axis oriented to a bottom of the periodontal pocket when the head portion is positioned near the periodontal pocket;

a first optical guide having one end positioned for receiving an emitted beam and another end in coincidence with the first optical axis for directing the beam through the first lens;

a second lens located in the head portion and having a second optical axis crossing the first optical axis at a set point;

a second optical guide having one end in opposition to the second lens in the head portion and extending along a radial direction of the second lens, one end of the second optical guide having a central position and a receiving position at which the beam reflected at the bottom of the periodontal pocket is set to be received; and analyzing means for receiving signals from the other end of the second optical guide so as to calculate the depth of the periodontal pocket on the basis of triangulation.

6. A probe as set forth in claim 5, wherein the analyzing means comprises means for calculation of the depth of the periodontal pocket using a distance between the set point and a bottom of the head portion, the angle between said optical paths, the central position and a distance between the central position and the receiving position.

7. A probe as set forth in claim 5 further comprising a projection provided to the head portion so as to be engaged with a tooth along which the periodontal pocket is generated.

8. A probe as set forth in claim 5 further comprising an air nozzle terminated in the head portion so as to aim at the periodontal pocket.

9. A probe as set forth in claim 5, wherein the head portion is movable in any direction.

10. A probe as set forth in claim 5, wherein the analyzing means includes a numeric display for displaying the depth of the periodontal pocket.

11. A probe for measuring a depth of a periodontal pocket, comprising:

emitting means for emitting a light beam from a position at a distance from the periodontal pocket toward the periodontal pocket so that the light beam may be reflected on a bottom of the periodontal pocket;

receiving means at a position at another distance from the periodontal pocket for receiving the reflected light beam;

analyzing means for determining the depth of the periodontal pocket on the basis of the light beam received at the receiving means; and a first polarizing plate and a second polarizing plate whose polarizing axes are crossed at right angles, the first polarizing plate being positioned between the emitting means and the periodontal pocket, the second polarizing plate being positioned between the periodontal pocket and the receiving means.

* * * * *